(12) United States Patent
Wallace et al.

(10) Patent No.: US 11,331,187 B2
(45) Date of Patent: May 17, 2022

(54) CARDIAC VALVE DELIVERY DEVICES AND SYSTEMS

(71) Applicant: CEPHEA VALVE TECHNOLOGIES, INC., San Jose, CA (US)

(72) Inventors: Dan Wallace, Santa Cruz, CA (US); Peter Gregg, Santa Cruz, CA (US); Evelyn Haynes, Santa Cruz, CA (US); Aaron Grogan, Scotts Valley, CA (US); Crissly Crisostomo, Santa Cruz, CA (US)

(73) Assignee: Cephea Valve Technologies, Inc., Santa Clara, CA (US)

( * ) Notice: Subject to any disclaimer, the term of this patent is extended or adjusted under 35 U.S.C. 154(b) by 621 days.

(21) Appl. No.: 16/310,499

(22) PCT Filed: Jun. 16, 2017

(86) PCT No.: PCT/US2017/037850
§ 371 (c)(1),
(2) Date: Dec. 17, 2018

(87) PCT Pub. No.: WO2017/218877
PCT Pub. Date: Dec. 21, 2017

(65) Prior Publication Data
US 2019/0247188 A1    Aug. 15, 2019

Related U.S. Application Data

(60) Provisional application No. 62/424,021, filed on Nov. 18, 2016, provisional application No. 62/351,860, filed on Jun. 17, 2016.

(51) Int. Cl.
*A61F 2/24* (2006.01)
*A61M 29/00* (2006.01)
*A61B 17/08* (2006.01)
*A61F 2/95* (2013.01)

(52) U.S. Cl.
CPC ............ *A61F 2/2439* (2013.01); *A61B 17/08* (2013.01); *A61F 2/2436* (2013.01); *A61M 29/00* (2013.01); *A61F 2/9517* (2020.05)

(58) Field of Classification Search
CPC .... A61F 2/2436; A61F 2/2439; A61F 2/2427; A61F 2/243; A61F 2/2433; A61B 17/0467
See application file for complete search history.

(56) References Cited

U.S. PATENT DOCUMENTS

| | | |
|---|---|---|
| 3,334,629 A | 8/1967 | Cohn |
| 3,409,013 A | 11/1968 | Henry |

(Continued)

FOREIGN PATENT DOCUMENTS

| | | |
|---|---|---|
| CA | 2859666 A1 | 6/2013 |
| CN | 1338951 A | 3/2002 |

(Continued)

OTHER PUBLICATIONS

Extended European Search Report including Written Opinion for Application No. EP17814158.6, dated Jan. 15, 2020, pp. 1-8.

(Continued)

*Primary Examiner* — Wade Miles
(74) *Attorney, Agent, or Firm* — Lerner, David, Littenberg, Krumholz & Mentlik, LLP

(57) ABSTRACT

A delivery device includes a central elongate structure, a sheath, a plurality of tethers extending through the central elongate structure configured to hold a cardiac valve, a cutting mechanism, a handle, and a control. The sheath is configured to slide over the central elongate structure. The cutting mechanism is configured to cut the tethers upon activation to release the cardiac valve. The handle is connected to the central elongate structure. The control on the handle is configured to activate the cutting mechanism.

11 Claims, 27 Drawing Sheets

(56) References Cited

U.S. PATENT DOCUMENTS

| | | |
|---|---|---|
| 3,540,431 A | 11/1970 | Mobin-Uddin |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 4,056,854 A | 11/1977 | Boretos et al. |
| 4,106,129 A | 8/1978 | Carpentier et al. |
| 4,233,690 A | 11/1980 | Akins |
| 4,291,420 A | 9/1981 | Reul |
| 4,326,306 A | 4/1982 | Poler |
| 4,423,809 A | 1/1984 | Mazzocco |
| 4,425,908 A | 1/1984 | Simon |
| 4,501,030 A | 2/1985 | Lane |
| 4,531,943 A | 7/1985 | Van Tassel et al. |
| 4,580,568 A | 4/1986 | Gianturco |
| 4,602,911 A | 7/1986 | Ahmadi et al. |
| 4,610,688 A | 9/1986 | Silvestrini et al. |
| 4,617,932 A | 10/1986 | Kornberg |
| 4,648,881 A | 3/1987 | Carpentier et al. |
| 4,655,218 A | 4/1987 | Kulik et al. |
| 4,655,771 A | 4/1987 | Wallsten |
| 4,662,885 A | 5/1987 | DiPisa, Jr. |
| 4,665,906 A | 5/1987 | Jervis |
| 4,710,192 A | 12/1987 | Liotta et al. |
| 4,733,665 A | 3/1988 | Palmaz |
| 4,755,181 A | 7/1988 | Igoe |
| 4,796,629 A | 1/1989 | Grayzel |
| 4,819,751 A | 4/1989 | Shimada et al. |
| 4,834,755 A | 5/1989 | Silvestrini et al. |
| 4,856,516 A | 8/1989 | Hillstead |
| 4,865,600 A | 9/1989 | Carpentier et al. |
| 4,872,874 A | 10/1989 | Taheri |
| 4,873,978 A | 10/1989 | Ginsburg |
| 4,909,252 A | 3/1990 | Goldberger |
| 4,917,102 A | 4/1990 | Miller et al. |
| 4,927,426 A | 5/1990 | Dretler |
| 4,986,830 A | 1/1991 | Owens et al. |
| 4,994,077 A | 2/1991 | Dobben |
| 5,002,556 A | 3/1991 | Ishida et al. |
| 5,002,559 A | 3/1991 | Tower |
| 5,064,435 A | 11/1991 | Porter |
| 5,161,547 A | 11/1992 | Tower |
| 5,163,953 A | 11/1992 | Vince |
| 5,209,741 A | 5/1993 | Spaeth |
| 5,258,023 A | 11/1993 | Reger |
| 5,258,042 A | 11/1993 | Mehta |
| 5,332,402 A | 7/1994 | Teitelbaum |
| 5,336,258 A | 8/1994 | Quintero et al. |
| 5,350,398 A | 9/1994 | Pavcnik et al. |
| 5,370,685 A | 12/1994 | Stevens |
| 5,389,106 A | 2/1995 | Tower |
| 5,397,351 A | 3/1995 | Pavcnik et al. |
| 5,405,377 A | 4/1995 | Cragg |
| 5,411,552 A | 5/1995 | Andersen et al. |
| 5,425,762 A | 6/1995 | Muller |
| 5,431,676 A | 7/1995 | Dubrul et al. |
| 5,443,495 A | 8/1995 | Buscemi et al. |
| 5,443,499 A | 8/1995 | Schmitt |
| 5,476,506 A | 12/1995 | Lunn |
| 5,476,510 A | 12/1995 | Eberhardt et al. |
| 5,480,423 A | 1/1996 | Ravenscroft et al. |
| 5,507,767 A | 4/1996 | Maeda et al. |
| 5,534,007 A | 7/1996 | St. Germain et al. |
| 5,545,133 A | 8/1996 | Burns et al. |
| 5,545,211 A | 8/1996 | An et al. |
| 5,549,665 A | 8/1996 | Vesely et al. |
| 5,554,183 A | 9/1996 | Nazari |
| 5,554,185 A | 9/1996 | Block et al. |
| 5,571,215 A | 11/1996 | Sterman et al. |
| 5,573,520 A | 11/1996 | Schwartz et al. |
| 5,575,818 A | 11/1996 | Pinchuk |
| 5,645,559 A | 7/1997 | Hachtman et al. |
| 5,662,671 A | 9/1997 | Barbut et al. |
| 5,667,523 A | 9/1997 | Bynon et al. |
| 5,674,277 A | 10/1997 | Freitag |
| 5,693,083 A | 12/1997 | Baker et al. |
| 5,695,498 A | 12/1997 | Tower |
| 5,713,953 A | 2/1998 | Vallana et al. |
| 5,716,370 A | 2/1998 | Williamson et al. |
| 5,720,391 A | 2/1998 | Dohm et al. |
| 5,725,552 A | 3/1998 | Kotula et al. |
| 5,733,325 A | 3/1998 | Robinson et al. |
| 5,735,842 A | 4/1998 | Krueger et al. |
| 5,769,812 A | 6/1998 | Stevens et al. |
| 5,807,405 A | 9/1998 | Vanney et al. |
| 5,817,126 A | 10/1998 | Imran |
| 5,824,041 A | 10/1998 | Lenker et al. |
| 5,824,043 A | 10/1998 | Cottone, Jr. |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,064 A | 10/1998 | Taheri |
| 5,843,158 A | 12/1998 | Lenker et al. |
| 5,855,597 A | 1/1999 | Jayaraman |
| 5,855,601 A | 1/1999 | Bessler et al. |
| 5,860,966 A | 1/1999 | Tower |
| 5,861,024 A | 1/1999 | Rashidi |
| 5,861,028 A | 1/1999 | Angell |
| 5,868,783 A | 2/1999 | Tower |
| 5,876,448 A | 3/1999 | Thompson et al. |
| 5,885,228 A | 3/1999 | Rosenman et al. |
| 5,888,201 A | 3/1999 | Stinson et al. |
| 5,891,191 A | 4/1999 | Stinson |
| 5,895,399 A | 4/1999 | Barbut et al. |
| 5,907,893 A | 6/1999 | Zadno-Azizi et al. |
| 5,911,734 A | 6/1999 | Tsugita et al. |
| 5,925,063 A | 7/1999 | Khosravi |
| 5,944,738 A | 8/1999 | Amplatz et al. |
| 5,954,766 A | 9/1999 | Zadno-Azizi et al. |
| 5,957,949 A | 9/1999 | Leonhardt et al. |
| 5,957,973 A | 9/1999 | Quiachon et al. |
| 5,968,070 A | 10/1999 | Bley et al. |
| 5,984,957 A | 11/1999 | Laptewicz et al. |
| 5,984,959 A | 11/1999 | Robertson et al. |
| 5,984,973 A | 11/1999 | Girard et al. |
| 5,993,469 A | 11/1999 | McKenzie et al. |
| 5,997,557 A | 12/1999 | Barbut et al. |
| 6,010,522 A | 1/2000 | Barbut et al. |
| 6,022,370 A | 2/2000 | Tower |
| 6,027,525 A | 2/2000 | Suh et al. |
| 6,042,598 A | 3/2000 | Tsugita et al. |
| 6,042,607 A | 3/2000 | Williamson et al. |
| 6,093,203 A | 7/2000 | Uflacker |
| 6,113,612 A | 9/2000 | Swanson et al. |
| 6,123,723 A | 9/2000 | Konya et al. |
| 6,142,987 A | 11/2000 | Tsugita |
| 6,162,245 A | 12/2000 | Jayaraman |
| 6,165,209 A | 12/2000 | Patterson et al. |
| 6,168,579 B1 | 1/2001 | Tsugita |
| 6,171,327 B1 | 1/2001 | Daniel et al. |
| 6,174,322 B1 | 1/2001 | Schneidt |
| 6,179,859 B1 | 1/2001 | Bates et al. |
| 6,187,016 B1 | 2/2001 | Hedges et al. |
| 6,197,053 B1 | 3/2001 | Cosgrove et al. |
| 6,200,336 B1 | 3/2001 | Pavcnik et al. |
| 6,206,909 B1 | 3/2001 | Hanada et al. |
| 6,214,036 B1 | 4/2001 | Letendre et al. |
| 6,221,006 B1 | 4/2001 | Dubrul et al. |
| 6,221,096 B1 | 4/2001 | Aiba et al. |
| 6,231,544 B1 | 5/2001 | Tsugita et al. |
| 6,231,551 B1 | 5/2001 | Barbut |
| 6,241,757 B1 | 6/2001 | An et al. |
| 6,245,102 B1 | 6/2001 | Jayaraman |
| 6,251,135 B1 | 6/2001 | Stinson et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,277,555 B1 | 8/2001 | Duran et al. |
| 6,309,417 B1 | 10/2001 | Spence et al. |

| Patent No. | Date | Inventor(s) |
|---|---|---|
| 6,312,465 B1 | 11/2001 | Griffin et al. |
| 6,319,281 B1 | 11/2001 | Patel |
| 6,336,934 B1 | 1/2002 | Gilson et al. |
| 6,336,937 B1 | 1/2002 | Vonesh et al. |
| 6,338,735 B1 | 1/2002 | Stevens |
| 6,348,063 B1 | 2/2002 | Yassour et al. |
| 6,352,708 B1 | 3/2002 | Duran et al. |
| 6,361,545 B1 | 3/2002 | Macoviak et al. |
| 6,371,970 B1 | 4/2002 | Khosravi et al. |
| 6,371,983 B1 | 4/2002 | Lane |
| 6,379,368 B1 | 4/2002 | Corcoran et al. |
| 6,379,383 B1 | 4/2002 | Palmaz et al. |
| 6,398,807 B1 | 6/2002 | Chouinard et al. |
| 6,409,750 B1 | 6/2002 | Hyodoh et al. |
| 6,411,552 B1 | 6/2002 | Chiba |
| 6,416,510 B1 | 7/2002 | Altman et al. |
| 6,419,696 B1 | 7/2002 | Ortiz et al. |
| 6,425,916 B1 | 7/2002 | Garrison et al. |
| 6,440,152 B1 | 8/2002 | Gainor et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,468,303 B1 | 10/2002 | Amplatz et al. |
| 6,475,239 B1 | 11/2002 | Campbell et al. |
| 6,482,228 B1 | 11/2002 | Norred |
| 6,485,502 B2 | 11/2002 | Don Michael et al. |
| 6,494,909 B2 | 12/2002 | Greenhalgh |
| 6,503,272 B2 | 1/2003 | Duerig et al. |
| 6,527,800 B1 | 3/2003 | McGuckin et al. |
| 6,540,768 B1 | 4/2003 | Diaz et al. |
| 6,562,058 B2 | 5/2003 | Seguin et al. |
| 6,592,546 B1 | 7/2003 | Barbut et al. |
| 6,592,614 B2 | 7/2003 | Lenker et al. |
| 6,610,077 B1 | 8/2003 | Hancock et al. |
| 6,616,675 B1 | 9/2003 | Evard et al. |
| 6,616,682 B2 | 9/2003 | Joergensen et al. |
| 6,622,604 B1 | 9/2003 | Chouinard et al. |
| 6,623,518 B2 | 9/2003 | Thompson et al. |
| 6,635,068 B1 | 10/2003 | Dubrul et al. |
| 6,635,079 B2 | 10/2003 | Unsworth et al. |
| 6,652,571 B1 | 11/2003 | White et al. |
| 6,656,206 B2 | 12/2003 | Corcoran et al. |
| 6,663,588 B2 | 12/2003 | DuBois et al. |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,668 B2 | 1/2004 | Mercereau et al. |
| 6,676,692 B2 | 1/2004 | Rabkin et al. |
| 6,676,698 B2 | 1/2004 | McGuckin et al. |
| 6,682,558 B2 | 1/2004 | Tu et al. |
| 6,682,559 B2 | 1/2004 | Myers et al. |
| 6,689,144 B2 | 2/2004 | Gerberding |
| 6,689,164 B1 | 2/2004 | Seguin |
| 6,692,512 B2 | 2/2004 | Jang |
| 6,695,864 B2 | 2/2004 | Macoviak et al. |
| 6,695,865 B2 | 2/2004 | Boyle et al. |
| 6,702,851 B1 | 3/2004 | Chinn et al. |
| 6,712,836 B1 | 3/2004 | Berg et al. |
| 6,712,842 B1 | 3/2004 | Gifford et al. |
| 6,712,843 B2 | 3/2004 | Elliott |
| 6,714,842 B1 | 3/2004 | Ito |
| 6,723,122 B2 | 4/2004 | Yang et al. |
| 6,730,118 B2 | 5/2004 | Spenser et al. |
| 6,730,377 B2 | 5/2004 | Wang |
| 6,733,525 B2 | 5/2004 | Yang et al. |
| 6,752,828 B2 | 6/2004 | Thornton |
| 6,758,855 B2 | 7/2004 | Fulton et al. |
| 6,764,503 B1 | 7/2004 | Ishimaru |
| 6,764,509 B2 | 7/2004 | Chinn et al. |
| 6,767,345 B2 | 7/2004 | St. Germain et al. |
| 6,773,454 B2 | 8/2004 | Wholey et al. |
| 6,776,791 B1 | 8/2004 | Stallings et al. |
| 6,790,218 B2 | 9/2004 | Jayaraman |
| 6,790,229 B1 | 9/2004 | Berreklouw |
| 6,790,230 B2 | 9/2004 | Beyersdorf et al. |
| 6,790,237 B2 | 9/2004 | Stinson |
| 6,792,979 B2 | 9/2004 | Konya et al. |
| 6,814,746 B2 | 11/2004 | Thompson et al. |
| 6,821,297 B2 | 11/2004 | Snyders |
| 6,837,901 B2 | 1/2005 | Rabkin et al. |
| 6,843,802 B1 | 1/2005 | Villalobos et al. |
| 6,849,085 B2 | 2/2005 | Marton |
| 6,863,668 B2 | 3/2005 | Gillespie et al. |
| 6,872,223 B2 | 3/2005 | Roberts et al. |
| 6,872,226 B2 | 3/2005 | Cali et al. |
| 6,875,231 B2 | 4/2005 | Anduiza et al. |
| 6,881,220 B2 | 4/2005 | Edwin et al. |
| 6,887,266 B2 | 5/2005 | Williams et al. |
| 6,890,340 B2 | 5/2005 | Duane |
| 6,893,459 B1 | 5/2005 | Macoviak |
| 6,893,460 B2 | 5/2005 | Spenser et al. |
| 6,905,743 B1 | 6/2005 | Chen et al. |
| 6,908,481 B2 | 6/2005 | Cribier |
| 6,911,036 B2 | 6/2005 | Douk et al. |
| 6,911,037 B2 | 6/2005 | Gainor et al. |
| 6,913,614 B2 | 7/2005 | Marino et al. |
| 6,921,397 B2 | 7/2005 | Corcoran et al. |
| 6,936,058 B2 | 8/2005 | Forde et al. |
| 6,936,067 B2 | 8/2005 | Buchanan |
| 6,945,997 B2 | 9/2005 | Huynh et al. |
| 6,951,571 B1 | 10/2005 | Srivastava |
| 6,953,332 B1 | 10/2005 | Kurk et al. |
| 6,960,220 B2 | 11/2005 | Marino et al. |
| 6,960,224 B2 | 11/2005 | Marino et al. |
| 6,974,464 B2 | 12/2005 | Quijano et al. |
| 6,974,476 B2 | 12/2005 | McGuckin et al. |
| 6,979,350 B2 | 12/2005 | Moll et al. |
| 6,984,242 B2 | 1/2006 | Campbell et al. |
| 7,011,681 B2 | 3/2006 | Vesely |
| 7,018,406 B2 | 3/2006 | Seguin et al. |
| 7,025,791 B2 | 4/2006 | Levine et al. |
| 7,037,331 B2 | 5/2006 | Mitelberg et al. |
| 7,077,861 B2 | 7/2006 | Spence |
| 7,087,072 B2 | 8/2006 | Marino et al. |
| 7,115,135 B2 | 10/2006 | Corcoran et al. |
| 7,122,020 B2 | 10/2006 | Mogul |
| 7,144,410 B2 | 12/2006 | Marino et al. |
| 7,166,097 B2 | 1/2007 | Barbut |
| 7,175,653 B2 | 2/2007 | Gaber |
| 7,175,654 B2 | 2/2007 | Bonsignore et al. |
| 7,189,258 B2 | 3/2007 | Johnson et al. |
| 7,191,018 B2 | 3/2007 | Gielen et al. |
| 7,192,435 B2 | 3/2007 | Corcoran et al. |
| 7,201,772 B2 | 4/2007 | Schwammenthal et al. |
| 7,235,093 B2 | 6/2007 | Gregorich |
| 7,261,732 B2 | 8/2007 | Justino |
| 7,320,704 B2 | 1/2008 | Lashinski et al. |
| 7,329,279 B2 | 2/2008 | Haug et al. |
| 7,374,560 B2 | 5/2008 | Ressemann et al. |
| 7,381,219 B2 | 6/2008 | Salahieh et al. |
| 7,402,171 B2 | 7/2008 | Osborne et al. |
| 7,413,563 B2 | 8/2008 | Corcoran et al. |
| 7,445,631 B2 | 11/2008 | Salahieh et al. |
| 7,455,689 B2 | 11/2008 | Johnson |
| 7,566,336 B2 | 7/2009 | Corcoran et al. |
| 7,582,104 B2 | 9/2009 | Corcoran et al. |
| 7,591,848 B2 | 9/2009 | Allen |
| 7,625,364 B2 | 12/2009 | Corcoran et al. |
| 7,632,298 B2 | 12/2009 | Hijlkema et al. |
| 7,658,748 B2 | 2/2010 | Marino et al. |
| 7,691,115 B2 | 4/2010 | Corcoran et al. |
| 7,712,606 B2 | 5/2010 | Salahieh et al. |
| 7,722,666 B2 | 5/2010 | LaFontaine |
| 7,748,389 B2 | 7/2010 | Salahieh et al. |
| 7,749,238 B2 | 7/2010 | Corcoran et al. |
| 7,780,725 B2 | 8/2010 | Haug et al. |
| 7,803,184 B2 | 9/2010 | McGuckin et al. |
| 7,803,186 B1 | 9/2010 | Li et al. |
| 7,824,442 B2 | 11/2010 | Salahieh et al. |
| 7,824,443 B2 | 11/2010 | Salahieh et al. |
| 7,896,915 B2 | 3/2011 | Guyenot et al. |
| 7,905,901 B2 | 3/2011 | Corcoran et al. |
| 7,927,351 B2 | 4/2011 | Corcoran et al. |
| 7,972,361 B2 | 7/2011 | Corcoran et al. |
| 8,043,368 B2 | 10/2011 | Crabtree |
| 8,057,540 B2 | 11/2011 | Letac et al. |
| 8,092,520 B2 | 1/2012 | Quadri |

| | | |
|---|---|---|
| 8,167,935 B2 | 5/2012 | McGuckin et al. |
| 8,236,049 B2 | 8/2012 | Rowe et al. |
| 8,317,858 B2 | 11/2012 | Straubinger et al. |
| 8,366,741 B2 | 2/2013 | Chin et al. |
| 8,398,708 B2 | 3/2013 | Meiri et al. |
| 8,425,593 B2 | 4/2013 | Braido et al. |
| 8,444,689 B2 | 5/2013 | Zhang |
| 8,449,599 B2 | 5/2013 | Chau et al. |
| 8,551,132 B2 | 10/2013 | Eskridge et al. |
| 8,551,161 B2 | 10/2013 | Dolan |
| 8,562,672 B2 | 10/2013 | Bonhoeffer et al. |
| 8,568,475 B2 | 10/2013 | Nguyen et al. |
| 8,579,964 B2 | 11/2013 | Lane et al. |
| 8,579,966 B2 | 11/2013 | Seguin et al. |
| 8,623,074 B2 | 1/2014 | Ryan |
| 8,628,566 B2 | 1/2014 | Eberhardt et al. |
| 8,673,000 B2 | 3/2014 | Tabor et al. |
| 8,685,080 B2 | 4/2014 | White |
| 8,721,708 B2 | 5/2014 | Sèguin et al. |
| 8,728,155 B2 | 5/2014 | Montorfano et al. |
| 8,740,962 B2 | 6/2014 | Finch et al. |
| 8,795,356 B2 | 8/2014 | Quadri et al. |
| 8,801,779 B2 | 8/2014 | Seguin et al. |
| 8,845,722 B2 | 9/2014 | Gabbay |
| 8,852,272 B2 | 10/2014 | Gross et al. |
| 8,870,948 B1 | 10/2014 | Erzberger et al. |
| 8,894,702 B2 | 11/2014 | Quadri et al. |
| 8,911,455 B2 | 12/2014 | Quadri et al. |
| 8,956,404 B2 | 2/2015 | Börtlein et al. |
| 8,986,375 B2 | 3/2015 | Garde et al. |
| 8,998,976 B2 | 4/2015 | Gregg et al. |
| 9,011,527 B2 | 4/2015 | Li et al. |
| 9,017,399 B2 | 4/2015 | Gross et al. |
| 9,023,074 B2 | 5/2015 | Theobald et al. |
| 9,023,100 B2 | 5/2015 | Quadri et al. |
| 9,034,032 B2 | 5/2015 | McLean et al. |
| 9,039,757 B2 | 5/2015 | McLean et al. |
| 9,060,857 B2 | 6/2015 | Nguyen et al. |
| 9,101,467 B2 | 8/2015 | Eberhardt et al. |
| 9,125,740 B2 | 9/2015 | Morriss et al. |
| 9,132,009 B2 | 9/2015 | Hacohen et al. |
| 9,155,617 B2 | 10/2015 | Carpentier et al. |
| 9,168,130 B2 | 10/2015 | Straubinger et al. |
| 9,168,131 B2 | 10/2015 | Yohanan et al. |
| 9,232,994 B2 | 1/2016 | Miller |
| 9,387,071 B2 | 7/2016 | Tuval et al. |
| 9,393,110 B2 | 7/2016 | Levi et al. |
| 9,393,112 B2 | 7/2016 | Tuval et al. |
| 9,414,852 B2 | 8/2016 | Gifford et al. |
| 9,414,913 B2 | 8/2016 | Beith et al. |
| 9,421,083 B2 | 8/2016 | Eidenschink et al. |
| 9,421,098 B2 | 8/2016 | Gifford et al. |
| 9,439,757 B2 | 9/2016 | Granada et al. |
| 9,474,605 B2 | 10/2016 | Rowe et al. |
| 9,474,609 B2 | 10/2016 | Haverkost et al. |
| 9,480,556 B2 | 11/2016 | Revuelta et al. |
| 9,480,558 B2 | 11/2016 | Destefano |
| 9,480,563 B2 | 11/2016 | Li |
| 9,486,306 B2 | 11/2016 | Tegels et al. |
| 9,492,273 B2 | 11/2016 | Granada et al. |
| 9,498,330 B2 | 11/2016 | Solem |
| 9,504,564 B2 | 11/2016 | Nguyen et al. |
| 9,504,568 B2 | 11/2016 | Ryan et al. |
| 9,510,943 B2 | 12/2016 | Mesana et al. |
| 9,554,899 B2 | 1/2017 | Granada et al. |
| 9,561,103 B2 | 2/2017 | Granada et al. |
| 9,579,198 B2 | 2/2017 | Deem et al. |
| 9,655,722 B2 | 5/2017 | Morriss et al. |
| 9,883,941 B2 | 2/2018 | Hastings et al. |
| 9,949,824 B2 | 4/2018 | Bonhoeffer et al. |
| 10,004,601 B2 | 6/2018 | Tuval et al. |
| 10,143,552 B2 | 12/2018 | Wallace et al. |
| 10,149,761 B2 | 12/2018 | Granada et al. |
| 10,154,906 B2 | 12/2018 | Granada et al. |
| 10,500,038 B1 * | 12/2019 | Orlov .................. A61F 2/2427 |
| 2001/0007956 A1 | 7/2001 | Letac et al. |
| 2001/0039450 A1 | 11/2001 | Pavcnik et al. |
| 2001/0041928 A1 | 11/2001 | Pavcnik et al. |
| 2001/0041930 A1 | 11/2001 | Globerman et al. |
| 2001/0044652 A1 | 11/2001 | Moore |
| 2001/0044656 A1 | 11/2001 | Williamson et al. |
| 2002/0002396 A1 | 1/2002 | Fulkerson |
| 2002/0010489 A1 | 1/2002 | Grayzel et al. |
| 2002/0026233 A1 | 2/2002 | Shaknovich |
| 2002/0029981 A1 | 3/2002 | Nigam |
| 2002/0032481 A1 | 3/2002 | Gabbay |
| 2002/0055769 A1 | 5/2002 | Wang |
| 2002/0062135 A1 | 5/2002 | Mazzocchi et al. |
| 2002/0082609 A1 | 6/2002 | Green |
| 2002/0095173 A1 | 7/2002 | Mazzocchi et al. |
| 2002/0120328 A1 | 8/2002 | Pathak et al. |
| 2002/0161392 A1 | 10/2002 | Dubrul |
| 2002/0161394 A1 | 10/2002 | Macoviak et al. |
| 2002/0177766 A1 | 11/2002 | Mogul |
| 2002/0183781 A1 | 12/2002 | Casey et al. |
| 2002/0188341 A1 | 12/2002 | Elliott |
| 2002/0188344 A1 | 12/2002 | Bolea et al. |
| 2003/0023303 A1 | 1/2003 | Palmaz et al. |
| 2003/0036791 A1 | 2/2003 | Philipp et al. |
| 2003/0040771 A1 | 2/2003 | Hyodoh et al. |
| 2003/0040772 A1 | 2/2003 | Hyodoh et al. |
| 2003/0040791 A1 | 2/2003 | Oktay |
| 2003/0050694 A1 | 3/2003 | Yang et al. |
| 2003/0055495 A1 | 3/2003 | Pease et al. |
| 2003/0060844 A1 | 3/2003 | Borillo et al. |
| 2003/0070944 A1 | 4/2003 | Nigam |
| 2003/0074011 A1 | 4/2003 | Gilboa et al. |
| 2003/0109924 A1 | 6/2003 | Cribier |
| 2003/0109930 A1 | 6/2003 | Bluni et al. |
| 2003/0114912 A1 | 6/2003 | Sequin et al. |
| 2003/0130729 A1 | 7/2003 | Paniagua et al. |
| 2003/0135257 A1 | 7/2003 | Taheri |
| 2003/0144732 A1 | 7/2003 | Cosgrove et al. |
| 2003/0149476 A1 | 8/2003 | Damm et al. |
| 2003/0149477 A1 | 8/2003 | Gabbay |
| 2003/0149478 A1 | 8/2003 | Figulla et al. |
| 2003/0176884 A1 | 9/2003 | Berrada et al. |
| 2003/0181850 A1 | 9/2003 | Diamond et al. |
| 2003/0187495 A1 | 10/2003 | Cully et al. |
| 2003/0199971 A1 | 10/2003 | Tower et al. |
| 2003/0208224 A1 | 11/2003 | Broome |
| 2003/0212429 A1 | 11/2003 | Keegan et al. |
| 2003/0212454 A1 | 11/2003 | Scott et al. |
| 2003/0216774 A1 | 11/2003 | Larson |
| 2003/0225421 A1 | 12/2003 | Peavey et al. |
| 2003/0225445 A1 | 12/2003 | Derus et al. |
| 2003/0229390 A1 | 12/2003 | Ashton et al. |
| 2003/0233117 A1 | 12/2003 | Adams et al. |
| 2004/0034411 A1 | 2/2004 | Quijano et al. |
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |
| 2004/0060563 A1 | 4/2004 | Rapacki et al. |
| 2004/0082904 A1 | 4/2004 | Houde et al. |
| 2004/0082967 A1 | 4/2004 | Broome et al. |
| 2004/0087982 A1 | 5/2004 | Eskuri |
| 2004/0093016 A1 | 5/2004 | Root et al. |
| 2004/0098022 A1 | 5/2004 | Barone |
| 2004/0098099 A1 | 5/2004 | McCullagh et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0127936 A1 | 7/2004 | Salahieh et al. |
| 2004/0127979 A1 | 7/2004 | Wilson et al. |
| 2004/0133274 A1 | 7/2004 | Webler et al. |
| 2004/0138694 A1 | 7/2004 | Tran et al. |
| 2004/0143294 A1 | 7/2004 | Corcoran et al. |
| 2004/0148021 A1 | 7/2004 | Cartledge et al. |
| 2004/0153094 A1 | 8/2004 | Dunfee et al. |
| 2004/0158277 A1 | 8/2004 | Lowe et al. |
| 2004/0167565 A1 | 8/2004 | Beulke et al. |
| 2004/0181140 A1 | 9/2004 | Falwell et al. |
| 2004/0186563 A1 | 9/2004 | Lobbi |
| 2004/0204755 A1 | 10/2004 | Robin |
| 2004/0215331 A1 | 10/2004 | Chew et al. |
| 2004/0215339 A1 | 10/2004 | Drasler et al. |
| 2004/0220655 A1 | 11/2004 | Swanson et al. |

| | | |
|---|---|---|
| 2004/0225321 A1 | 11/2004 | Krolik et al. |
| 2004/0225354 A1 | 11/2004 | Allen et al. |
| 2004/0254636 A1 | 12/2004 | Flagle et al. |
| 2005/0033402 A1 | 2/2005 | Cully et al. |
| 2005/0070934 A1 | 3/2005 | Tanaka et al. |
| 2005/0075662 A1 | 4/2005 | Pedersen et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0090846 A1 | 4/2005 | Pedersen et al. |
| 2005/0096692 A1 | 5/2005 | Linder et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0100580 A1 | 5/2005 | Osborne et al. |
| 2005/0107822 A1 | 5/2005 | WasDyke |
| 2005/0113910 A1 | 5/2005 | Paniagua et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137691 A1 | 6/2005 | Salahieh et al. |
| 2005/0137692 A1 | 6/2005 | Haug et al. |
| 2005/0137694 A1 | 6/2005 | Haug et al. |
| 2005/0137696 A1 | 6/2005 | Salahieh et al. |
| 2005/0137697 A1 | 6/2005 | Salahieh et al. |
| 2005/0137701 A1 | 6/2005 | Salahieh et al. |
| 2005/0143809 A1 | 6/2005 | Salahieh et al. |
| 2005/0165352 A1 | 7/2005 | Henry et al. |
| 2005/0182486 A1 | 8/2005 | Gabbay |
| 2005/0197694 A1 | 9/2005 | Pai et al. |
| 2005/0197695 A1 | 9/2005 | Stacchino et al. |
| 2005/0203614 A1 | 9/2005 | Forster et al. |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0209580 A1 | 9/2005 | Freyman |
| 2005/0228472 A1 | 10/2005 | Case et al. |
| 2005/0251250 A1 | 11/2005 | Verhoeven et al. |
| 2005/0251251 A1 | 11/2005 | Cribier |
| 2005/0261759 A1 | 11/2005 | Lambrecht et al. |
| 2005/0267560 A1 | 12/2005 | Bates |
| 2005/0283962 A1 | 12/2005 | Boudjemline |
| 2005/0288766 A1 | 12/2005 | Plain et al. |
| 2006/0004439 A1 | 1/2006 | Spenser et al. |
| 2006/0004442 A1 | 1/2006 | Spenser et al. |
| 2006/0015168 A1 | 1/2006 | Gunderson |
| 2006/0058872 A1 | 3/2006 | Salahieh et al. |
| 2006/0116717 A1 | 6/2006 | Marino et al. |
| 2006/0122633 A1* | 6/2006 | To .................. A61B 17/0682 606/139 |
| 2006/0155312 A1 | 7/2006 | Levine et al. |
| 2006/0161249 A1 | 7/2006 | Realyvasquez et al. |
| 2006/0190030 A1 | 8/2006 | To et al. |
| 2006/0195183 A1 | 8/2006 | Navia et al. |
| 2006/0235510 A1 | 10/2006 | Johnson et al. |
| 2006/0247680 A1 | 11/2006 | Amplatz et al. |
| 2006/0253191 A1 | 11/2006 | Salahieh et al. |
| 2006/0259134 A1 | 11/2006 | Schwammenthal et al. |
| 2006/0259135 A1 | 11/2006 | Navia et al. |
| 2006/0259137 A1 | 11/2006 | Artof et al. |
| 2006/0265045 A1 | 11/2006 | Shiu et al. |
| 2006/0271166 A1 | 11/2006 | Thill et al. |
| 2006/0287668 A1 | 12/2006 | Fawzi et al. |
| 2007/0016286 A1 | 1/2007 | Herrmann et al. |
| 2007/0055340 A1 | 3/2007 | Pryor |
| 2007/0088431 A1 | 4/2007 | Bourang et al. |
| 2007/0100440 A1 | 5/2007 | Figulla et al. |
| 2007/0112355 A1 | 5/2007 | Salahieh et al. |
| 2007/0118214 A1 | 5/2007 | Salahieh et al. |
| 2007/0203503 A1 | 8/2007 | Salahieh et al. |
| 2007/0203575 A1 | 8/2007 | Forster et al. |
| 2007/0244552 A1 | 10/2007 | Salahieh et al. |
| 2007/0244556 A1* | 10/2007 | Rafiee .................. A61F 2/2451 623/2.11 |
| 2007/0255389 A1 | 11/2007 | Oberti et al. |
| 2007/0265656 A1 | 11/2007 | Amplatz et al. |
| 2007/0276324 A1 | 11/2007 | Laduca et al. |
| 2007/0288089 A1 | 12/2007 | Gurskis et al. |
| 2008/0015619 A1 | 1/2008 | Figulla et al. |
| 2008/0033543 A1 | 2/2008 | Gurskis et al. |
| 2008/0082165 A1 | 4/2008 | Wilson et al. |
| 2008/0140189 A1 | 6/2008 | Nguyen et al. |
| 2008/0140191 A1 | 6/2008 | Mathis et al. |
| 2008/0167682 A1 | 7/2008 | Corcoran et al. |
| 2008/0177381 A1 | 7/2008 | Navia et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0234797 A1 | 9/2008 | Styrc |
| 2008/0288054 A1 | 11/2008 | Pulnev et al. |
| 2009/0005863 A1 | 1/2009 | Goetz et al. |
| 2009/0062841 A1 | 3/2009 | Amplatz et al. |
| 2009/0082803 A1 | 3/2009 | Adams et al. |
| 2009/0093877 A1* | 4/2009 | Keidar .................. A61F 2/2427 623/2.11 |
| 2009/0171456 A1 | 7/2009 | Kveen et al. |
| 2009/0182405 A1 | 7/2009 | Arnault De La Menardiere et al. |
| 2009/0192585 A1 | 7/2009 | Bloom et al. |
| 2009/0222076 A1 | 9/2009 | Figulla et al. |
| 2009/0254165 A1 | 10/2009 | Tabor et al. |
| 2009/0264759 A1 | 10/2009 | Byrd |
| 2009/0287290 A1 | 11/2009 | Macaulay et al. |
| 2009/0306768 A1 | 12/2009 | Quadri |
| 2010/0036479 A1 | 2/2010 | Hill et al. |
| 2010/0049313 A1 | 2/2010 | Alon et al. |
| 2010/0094314 A1 | 4/2010 | Hernlund et al. |
| 2010/0114308 A1 | 5/2010 | Maschke |
| 2010/0121434 A1 | 5/2010 | Paul et al. |
| 2010/0161036 A1 | 6/2010 | Pintor et al. |
| 2010/0219092 A1 | 9/2010 | Salahieh et al. |
| 2010/0268204 A1 | 10/2010 | Tieu et al. |
| 2010/0280495 A1 | 11/2010 | Paul et al. |
| 2010/0284724 A1 | 11/2010 | Cardia |
| 2010/0298931 A1 | 11/2010 | Quadri et al. |
| 2010/0312333 A1 | 12/2010 | Navia et al. |
| 2011/0004296 A1 | 1/2011 | Lutter et al. |
| 2011/0022157 A1 | 1/2011 | Essinger et al. |
| 2011/0034987 A1 | 2/2011 | Kennedy |
| 2011/0166636 A1 | 7/2011 | Rowe |
| 2011/0218619 A1 | 9/2011 | Benichou et al. |
| 2011/0245911 A1 | 10/2011 | Quill et al. |
| 2011/0257723 A1 | 10/2011 | McNamara |
| 2011/0264198 A1 | 10/2011 | Murray et al. |
| 2011/0295363 A1 | 12/2011 | Girard et al. |
| 2011/0301702 A1 | 12/2011 | Rust et al. |
| 2012/0016464 A1 | 1/2012 | Seguin |
| 2012/0059458 A1 | 3/2012 | Buchbinder et al. |
| 2012/0078360 A1 | 3/2012 | Rafiee |
| 2012/0101572 A1 | 4/2012 | Kovalsky et al. |
| 2012/0158129 A1 | 6/2012 | Duffy et al. |
| 2012/0197283 A1 | 8/2012 | Marchand et al. |
| 2012/0197391 A1 | 8/2012 | Alkhatib et al. |
| 2013/0041447 A1 | 2/2013 | Erb et al. |
| 2013/0041458 A1 | 2/2013 | Lashinski et al. |
| 2013/0253643 A1 | 9/2013 | Rolando et al. |
| 2013/0261737 A1 | 10/2013 | Costello |
| 2013/0282110 A1 | 10/2013 | Schweich, Jr. et al. |
| 2013/0282114 A1 | 10/2013 | Schweich, Jr. et al. |
| 2013/0304197 A1 | 11/2013 | Buchbinder et al. |
| 2013/0310923 A1 | 11/2013 | Kheradvar et al. |
| 2013/0331931 A1 | 12/2013 | Gregg et al. |
| 2014/0005771 A1 | 1/2014 | Braido et al. |
| 2014/0005775 A1 | 1/2014 | Alkhatib et al. |
| 2014/0005778 A1 | 1/2014 | Buchbinder et al. |
| 2014/0012368 A1 | 1/2014 | Sugimoto et al. |
| 2014/0012374 A1 | 1/2014 | Rankin |
| 2014/0052237 A1 | 2/2014 | Lane et al. |
| 2014/0052241 A1 | 2/2014 | Harks et al. |
| 2014/0052244 A1 | 2/2014 | Rolando et al. |
| 2014/0067048 A1 | 3/2014 | Chau et al. |
| 2014/0081383 A1 | 3/2014 | Eberhardt et al. |
| 2014/0107665 A1 | 4/2014 | Shellenberger et al. |
| 2014/0128726 A1 | 5/2014 | Quill et al. |
| 2014/0180391 A1 | 6/2014 | Dagan et al. |

| | | | |
|---|---|---|---|
| 2014/0200649 A1* | 7/2014 | Essinger | A61F 2/2439 623/1.12 |
| 2014/0214157 A1 | 7/2014 | Bortlein et al. | |
| 2014/0214159 A1 | 7/2014 | Vidlund et al. | |
| 2014/0222136 A1 | 8/2014 | Geist et al. | |
| 2014/0236278 A1 | 8/2014 | Argentine et al. | |
| 2014/0243954 A1 | 8/2014 | Shannon | |
| 2014/0249622 A1 | 9/2014 | Carmi et al. | |
| 2014/0257476 A1 | 9/2014 | Montorfano et al. | |
| 2014/0277390 A1 | 9/2014 | Ratz et al. | |
| 2014/0277563 A1 | 9/2014 | White | |
| 2014/0324164 A1 | 10/2014 | Gross et al. | |
| 2014/0330368 A1 | 11/2014 | Gloss et al. | |
| 2014/0379076 A1 | 12/2014 | Vidlund et al. | |
| 2015/0039083 A1 | 2/2015 | Rafiee | |
| 2015/0045881 A1 | 2/2015 | Lim | |
| 2015/0094802 A1 | 4/2015 | Buchbinder et al. | |
| 2015/0112430 A1 | 4/2015 | Creaven et al. | |
| 2015/0119637 A1 | 4/2015 | Alvarez et al. | |
| 2015/0135506 A1 | 5/2015 | White | |
| 2015/0142100 A1 | 5/2015 | Morriss et al. | |
| 2015/0157457 A1 | 6/2015 | Hacohen | |
| 2015/0173897 A1 | 6/2015 | Raanani et al. | |
| 2015/0223773 A1 | 8/2015 | John et al. | |
| 2015/0302634 A1 | 10/2015 | Florent et al. | |
| 2015/0351903 A1 | 12/2015 | Morriss et al. | |
| 2015/0351904 A1 | 12/2015 | Cooper et al. | |
| 2016/0038280 A1 | 2/2016 | Morriss et al. | |
| 2016/0089234 A1 | 3/2016 | Gifford | |
| 2016/0151153 A1 | 6/2016 | Sandstrom et al. | |
| 2016/0158000 A1 | 6/2016 | Granada et al. | |
| 2016/0158003 A1 | 6/2016 | Wallace et al. | |
| 2016/0166384 A1 | 6/2016 | Olson et al. | |
| 2016/0310267 A1 | 10/2016 | Zeng et al. | |
| 2016/0310269 A1 | 10/2016 | Braido et al. | |
| 2017/0035569 A1 | 2/2017 | Deem et al. | |
| 2017/0042675 A1 | 2/2017 | Freudenthal | |
| 2017/0049571 A1 | 2/2017 | Gifford | |
| 2017/0209261 A1 | 7/2017 | Bortlein et al. | |
| 2017/0209269 A1 | 7/2017 | Conklin | |
| 2017/0231762 A1 | 8/2017 | Quadri et al. | |
| 2017/0325941 A1 | 11/2017 | Wallace et al. | |
| 2017/0360561 A1* | 12/2017 | Bell | A61F 2/852 |
| 2018/0000580 A1 | 1/2018 | Wallace et al. | |
| 2018/0056043 A1 | 3/2018 | Von Oepen et al. | |
| 2018/0092744 A1 | 4/2018 | von Oepen et al. | |
| 2018/0110622 A1 | 4/2018 | Gregg et al. | |
| 2018/0206983 A1 | 7/2018 | Noe et al. | |
| 2018/0206984 A1 | 7/2018 | Noe et al. | |
| 2018/0206985 A1 | 7/2018 | Noe et al. | |
| 2018/0206986 A1 | 7/2018 | Noe et al. | |
| 2018/0296325 A1 | 10/2018 | McLean | |
| 2018/0296335 A1 | 10/2018 | Miyashiro | |
| 2018/0296339 A1 | 10/2018 | McLean | |
| 2018/0296341 A1 | 10/2018 | Noe et al. | |
| 2018/0344454 A1* | 12/2018 | Mauch | A61F 2/844 |

FOREIGN PATENT DOCUMENTS

| | | |
|---|---|---|
| EP | 0409929 B1 | 4/1997 |
| EP | 1057459 A1 | 12/2000 |
| EP | 1057460 A1 | 12/2000 |
| EP | 0937439 B1 | 9/2003 |
| EP | 1340473 A2 | 9/2003 |
| EP | 1356793 A2 | 10/2003 |
| EP | 1042045 B1 | 5/2004 |
| EP | 0819013 B1 | 6/2004 |
| EP | 1229864 B1 | 4/2005 |
| EP | 1430853 A2 | 6/2005 |
| EP | 1059894 B1 | 7/2005 |
| EP | 1078610 B1 | 8/2005 |
| EP | 1469797 B1 | 11/2005 |
| EP | 1600121 A1 | 11/2005 |
| EP | 1616531 A2 | 1/2006 |
| EP | 1819304 A2 | 6/2006 |
| EP | 1849440 A1 | 10/2007 |
| EP | 2654624 A1 | 10/2013 |
| EP | 2124826 B1 | 7/2014 |
| WO | WO95/04556 A2 | 2/1995 |
| WO | WO95/29640 A1 | 11/1995 |
| WO | WO96/14032 A1 | 5/1996 |
| WO | WO96/24306 A1 | 8/1996 |
| WO | WO98/36790 A1 | 8/1998 |
| WO | WO98/57599 A2 | 12/1998 |
| WO | WO99/44542 A2 | 9/1999 |
| WO | WO00/09059 A2 | 2/2000 |
| WO | WO00/44308 A2 | 8/2000 |
| WO | WO00/44313 A1 | 8/2000 |
| WO | WO00/67661 A2 | 11/2000 |
| WO | WO01/05331 A1 | 1/2001 |
| WO | WO01/35870 A1 | 5/2001 |
| WO | WO01/64137 A1 | 9/2001 |
| WO | WO02/36048 A1 | 5/2002 |
| WO | WO02/41789 A2 | 5/2002 |
| WO | WO02/100297 A2 | 12/2002 |
| WO | WO03/003943 A2 | 1/2003 |
| WO | WO03/003949 A2 | 1/2003 |
| WO | WO03/011195 A2 | 2/2003 |
| WO | WO03/030776 A2 | 4/2003 |
| WO | WO03/015851 A1 | 11/2003 |
| WO | WO03/094797 A1 | 11/2003 |
| WO | WO2004/014256 A1 | 2/2004 |
| WO | WO2004/019811 A2 | 3/2004 |
| WO | WO2004/026117 A2 | 4/2004 |
| WO | WO2004/041126 A1 | 5/2004 |
| WO | WO2004/047681 A1 | 6/2004 |
| WO | WO2004/066876 A1 | 8/2004 |
| WO | WO2004/082536 A1 | 9/2004 |
| WO | WO2005/037361 A2 | 4/2005 |
| WO | WO2005/084595 A1 | 9/2005 |
| WO | WO2005/087140 A1 | 9/2005 |
| WO | WO2009/072122 A1 | 6/2009 |
| WO | WO2009/108615 A1 | 9/2009 |
| WO | WO2009/132187 A1 | 10/2009 |
| WO | WO2009/137755 A2 | 11/2009 |
| WO | WO2010/057262 A1 | 5/2010 |
| WO | WO2010/141847 A1 | 12/2010 |
| WO | WO2011/057087 A1 | 5/2011 |
| WO | WO2011/081997 A1 | 7/2011 |
| WO | WO2012/161786 A1 | 11/2012 |
| WO | WO2013/158608 A1 | 10/2013 |
| WO | WO2013/158613 A1 | 10/2013 |
| WO | WO2014/121280 A2 | 8/2014 |
| WO | WO2014/144247 A1 | 9/2014 |
| WO | 2015014960 A1 | 2/2015 |
| WO | WO2015/127283 A1 | 8/2015 |
| WO | WO2016/168609 A1 | 10/2016 |
| WO | WO2017/035002 A1 | 3/2017 |
| WO | WO2017/035434 A1 | 3/2017 |
| WO | WO2017/122109 A1 | 7/2017 |
| WO | WO2017/167759 A1 | 10/2017 |
| WO | WO2017/218877 A1 | 12/2017 |

OTHER PUBLICATIONS

Andersen et al.; Transluminal implantation of artificial heart valves. Description of a new expandable aortic valve and initial results with implantation by catheter technique in closed chest pigs; Euro. Heart J.; 13(5): 704-708; May 1992.

Atwood et al.; Insertion of Heart Valves by Catheterization; Project Supervised by Prof. S. Muftu of Northeastern University, May 2002: pp. 36-40.

Bodnar et al. Replacement Cardiac Valves; (Chapter 13) Extinct cardiac valve prostheses. Pergamon Publishing Corporation. New York, Aug. 1991: pp. 307-322.

Boudjemline et al. Percutaneous implantation of a biological valve in the aorta to treat aortic valve insufficiency—a sheep study.f Med Sci. Monit; Apr. 2002; vol. 8, No. 4: BR113-116.

Boudjemline et al. "Percutaneous implantation of a valve in the descending aorta in lambs." Euro. Heart J; Jul. 2002; 23: 1045-1049.

Boudjemline et al. "Percutaneous pulmonary valve replacement in a large right ventricular outflow tract: an experimental study." Journal of the Americal College of Cardiology; Mar. 2004; vol. 43(6): 1082-1087.

Boudjemline et al. "Percutaneous valve insertion: A new approach?" J. of Thoracic and Cardio. Surg; Mar. 2003; 125(3): 741-743.

Boudjemline et al. "Steps Toward Percutaneous Aortic Valve Replacement." Circulation; Feb. 2002; 105: 775-778.

Cribier et al. "Early Experience with Percutaneous Transcatheter Implantation of Heart Valve Prosthesis for the Treatment of End-Stage Inoperable Patients with Calcific Aortic Stenosis." J. of Am. Coll. of Cardio; Feb. 2004; 43(4): 698-703.

Cribier et al. "Percutaneous Transcatheter Implantation of an Aortic Valve Prosthesis for Calcific Aortic Stenosis: First Human Case Description." Circulation; Dec. 2002; 106: 3006-3008.

Cribier et al. "Percutaneous Transcatheter Implantation of an Aortic Valve Prosthesis for Calcific Aortic Stenosis: First Human Case." (slide presentation); TCT 2002 (conference); 16 pgs.; Washington D.C.; Sep. 24-28, 2002.

Ferrari et al. "Percutaneous transvascular aortic valve replacement with self expanding stent-valve device." Poster from the presentation given at SMIT 2000, 12th International Conference. 1 pg. Sep. 5, 2000.

Hijazi "Transcatheter Valve Replacement: A New Era of Percutaneous Cardiac Intervention Begins." J. of Am. College of Cardio; Mar. 2004; 43(6): 1088-1089.

Huber et al. "Do valved stents compromise coronary flow?" European Journal of Cardio-thoracic Surgery; May 2004; vol. 25: 754-759.

Knudsen et al. "Catheter-implanted prosthetic heart valves." Int'l J. of Art. Organs; May 1993; 16(5): 253-262.

Kort et al. "Minimally invasive aortic valve replacement: Echocardiographic and clinical results." Am. Heart J; Sep. 2001; 142(3): 476-481.

Love et al. fThe Autogenous Tissue Heart Valve: Current Stat.f Journal of Cardiac Surgery; Dec. 1991; 6(4): 499-507.

Lutter et al. "Percutaneous aortic valve replacement: An experimental study. I. Studies on implantation." J. of Thoracic and Cardio. Surg; Apr. 2002; 123(4): 768-776.

Moulopoulos et al. "Catheter-Mounted Aortic Valves." Annals of Thoracic Surg; May 1971; 11(5): 423-430.

Paniagua et al. "Percutaneous heart valve in the chronic in vitro testing model." Circulation; Sep. 2002; 106: e51-e52.

Paniagua et al. Heart Watch (2004). Texas Heart Institute. Spring Mar. 2004 Edition: 8 pages.

Pavcnik et al. "Percutaneous bioprosthetic veno valve: A long-term study in sheep." J. of Vascular Surg; Mar. 2002; 35(3): 598-603.

Phillips et al. "A Temporary Catheter-Tip Aortic Valve: Hemodynamic Effects on Experimental Acute Aortic Insufficiency." Annals of Thoracic Surg; Feb. 1976; 21(2): 134-136.

Sochman et al. "Percutaneous Transcatheter Aortic Disc Valve Prosthesis Implantation: A Feasibility Study." Cardiovasc. Intervent. Radiol; Sep.-Oct. 2000; 23: 384-388.

Solvay; Novel revivent (tm) Myocardial anchoring system from bioVentrix uses solvay's zeniva® PEEK in tether component; 3 pages retrieved from the internet (http://www.solvay.com/en/media/press_release/20131205-novel-revivent-myocardial-anchoring-system-bioventrix-uses-zenivapeek.html); (Press Release); on Aug. 10, 2017.

Stuart, M. "In Heart Valves, a Brave, New Non-Surgical World." Start-Up; Feb. 2004: 9-17.

Vahanian et al. "Percutaneous Approaches to Valvular Disease." Circulation; Apr. 2004; 109: 1572-1579.

Van Herwerden et al., "Percutaneous valve implantation: back to the future?" Euro. Heart J; Sep. 2002; 23(18): 1415-1416.

Zhou et al. "Self-expandable valved stent of large size: off-bypass implantation in pulmonary position." Eur. J. Cardiothorac; Aug. 2003; 24: 212-216.

Granada et al.; U.S. Appl. No. 16/224,221 entitled "System and method for cardiac valve repair and replacement," filed Dec. 18, 2018.

* cited by examiner

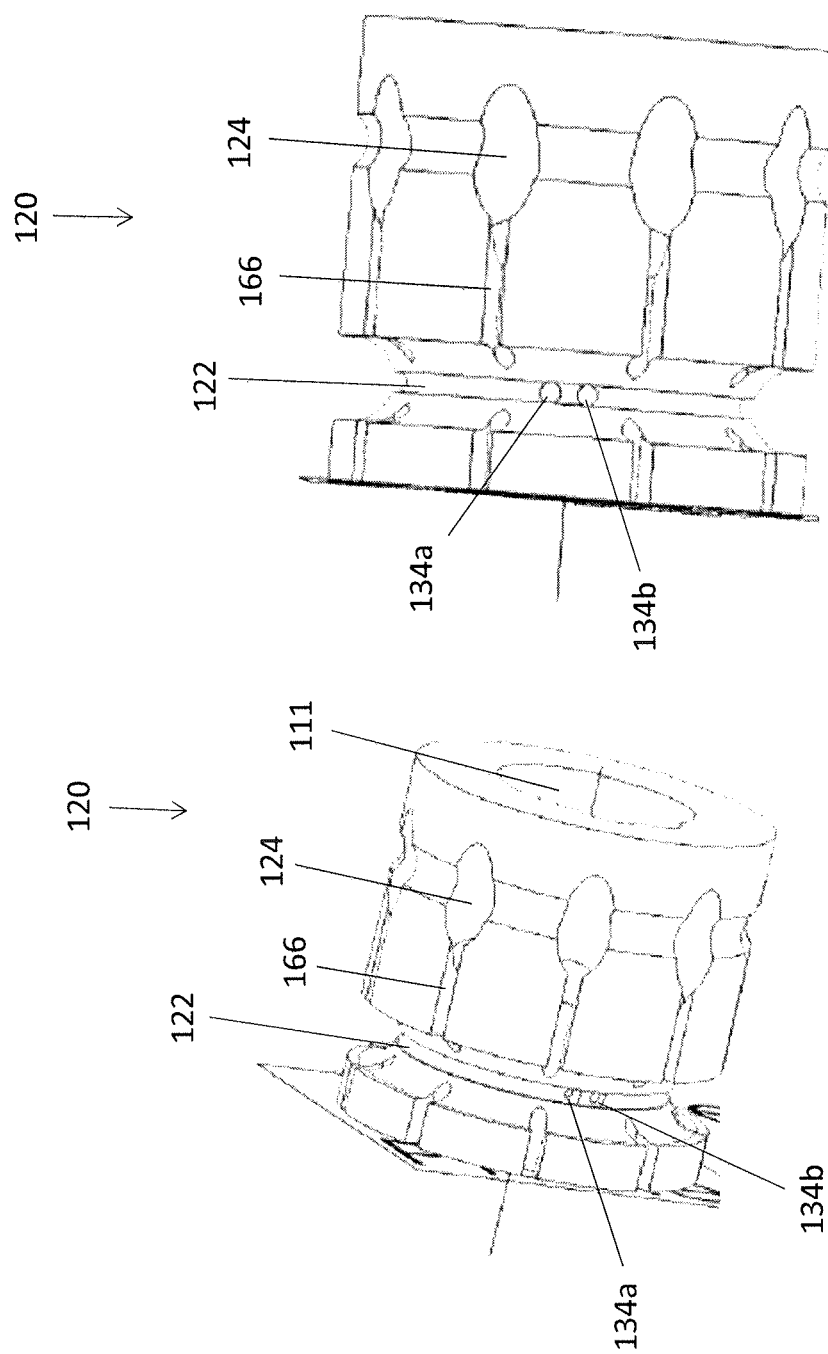

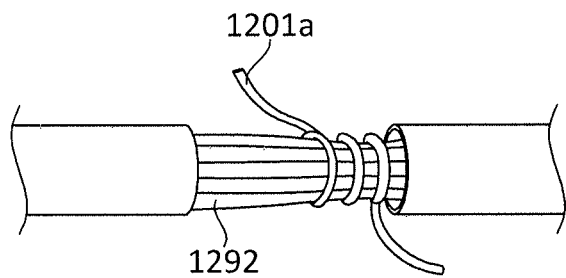
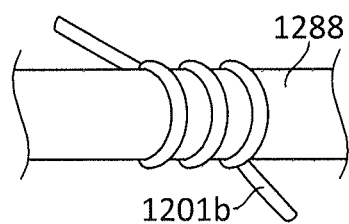
FIG. 12A
FIG. 12B
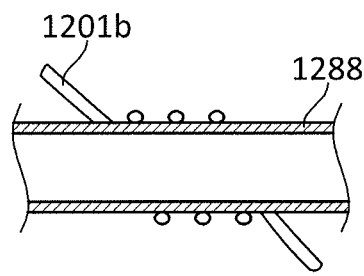
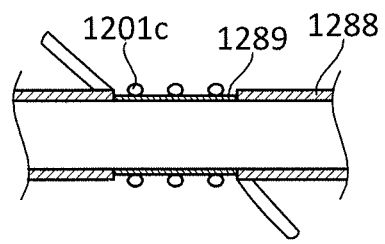
FIG. 12C
FIG. 12D

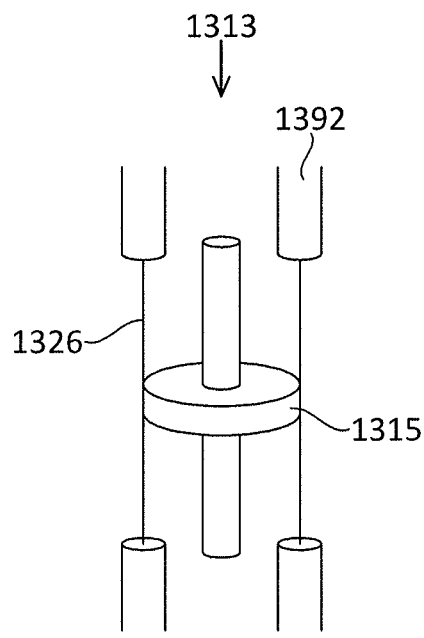
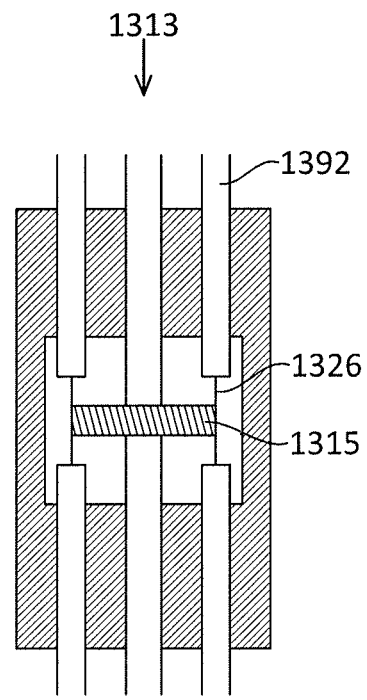
FIG. 13A
FIG. 13B
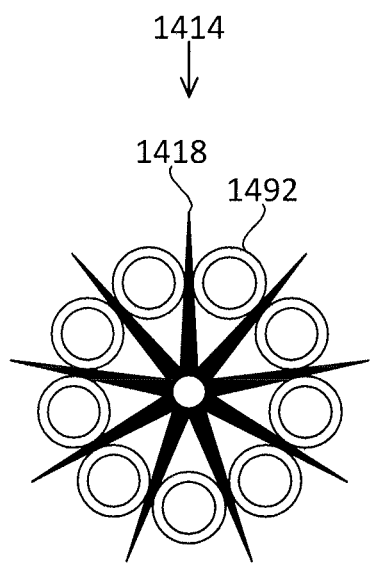
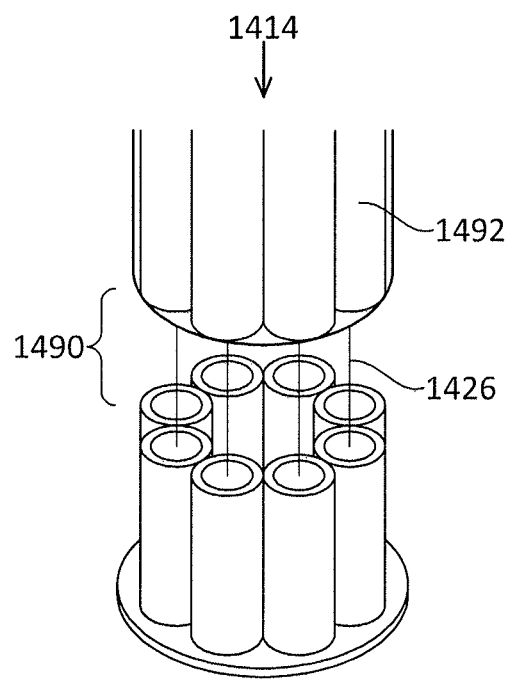
FIG. 14A
FIG. 14B

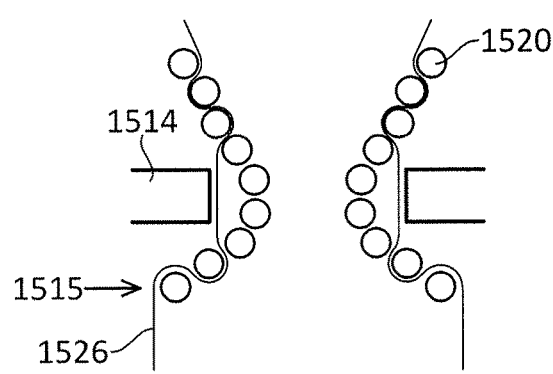
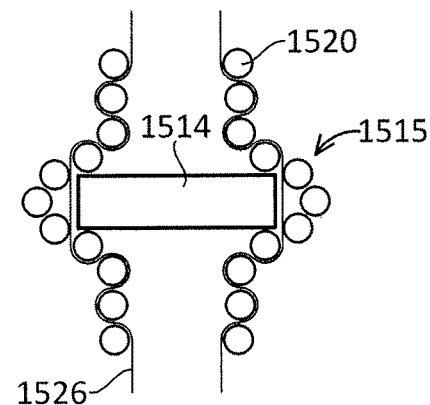
FIG. 15A
FIG. 15B
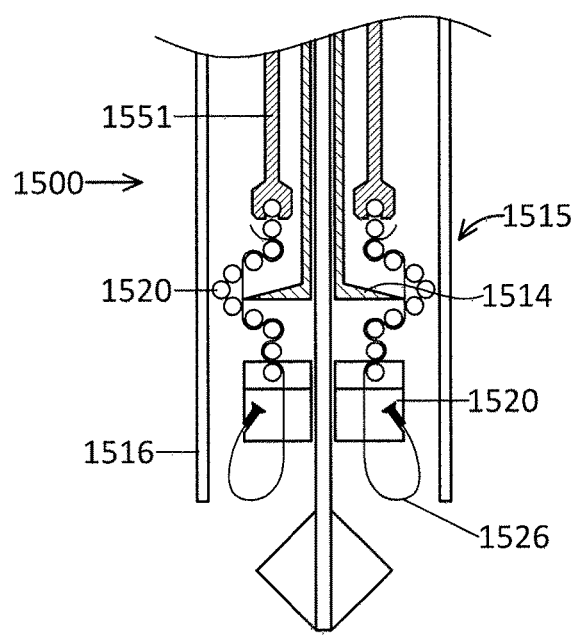
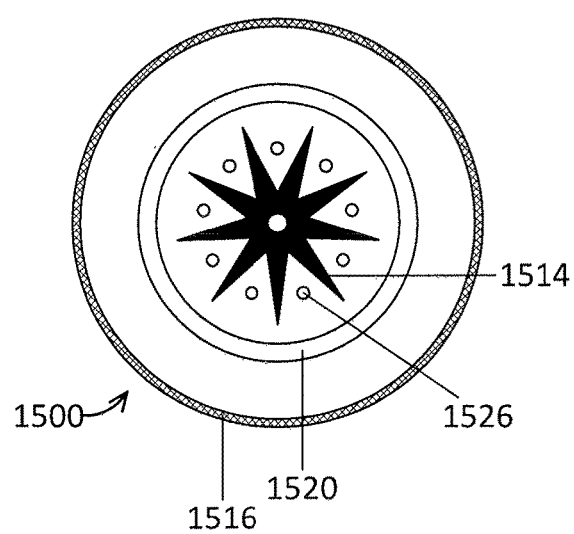
FIG. 15C
FIG. 15D

CARDIAC VALVE DELIVERY DEVICES AND SYSTEMS

CROSS REFERENCE TO RELATED APPLICATIONS

This application claims priority to U.S. Provisional Patent Application No. 62/351,860, filed Jun. 17, 2016, titled "CARDIAC VALVE DELIVERY DEVICES AND SYSTEMS, and U.S. Provisional Patent Application No. 62/424, 021 filed Nov. 18, 2016, titled "CARDIAC VALVE DELIVERY DEVICES AND SYSTEMS" the entireties of which are incorporated by reference herein.

This application may also be related to International Patent Application No. PCT/US2016/032546, titled "CARDIAC VALVE DELIVERY DEVICES AND SYSTEMS," filed May 13, 2016, the entirety of which is incorporated by reference herein.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present invention relates generally to the treatment of cardiac valve disorders, such as mitral valve replacement, using minimally invasive techniques. In particular, this application is directed towards devices for delivering and placing replacement mitral valves.

BACKGROUND

The mitral valve lies between the left atrium and the left ventricle of the heart. Various diseases can affect the function of the mitral valve, including degenerative mitral valve disease and mitral valve prolapse. These diseases can cause mitral stenosis, in which the valve fails to open fully and thereby obstructs blood flow, and/or mitral insufficiency, in which the mitral valve is incompetent and blood flows passively in the wrong direction.

Many patients with heart disease, such as problems with the mitral valve, are intolerant of the trauma associated with open-heart surgery. Age or advanced illness may have impaired the patient's ability to recover from the injury of an open-heart procedure. Additionally, the high costs associated with open-heart surgery and extra-corporeal perfusion can make such procedures prohibitive.

Patients in need of cardiac valve repair or cardiac valve replacement can be served by minimally invasive surgical techniques. In many minimally invasive procedures, small devices are manipulated within the patient's body under visualization from a live imaging source like ultrasound, fluoroscopy, or endoscopy. Minimally invasive cardiac procedures are inherently less traumatic than open procedures and may be performed without extra-corporeal perfusion, which carries a significant risk of procedural complications.

Prosthetic valve replacement procedures can be difficult, and various factors are generally taken into account when placing the valve. First, the prosthetic valve should be placed at the same or very nearly the same angle as the native valve. A valve that is off axis could cause turbulent blood flow and/or potential para-valvular leaks. Second, the prosthetic valve should ideally have concentricity. This means that the valve is placed in the same center as the native valve. An off center deployment or valve placement could affect the mechanism of neighboring valves or the heart's conductive system. Finally, the prosthetic valve should be at the proper depth within the patient's heart with respect to the location of the native valve, as otherwise, the prosthetic valve may interfere with the conductive nature of the heart as well.

A safe and efficient delivery system and method for replacement of a cardiac valve that addresses some or all of these concerns is described herein.

SUMMARY

In general, in one embodiment, a delivery device includes a central elongate structure, a sheath, a plurality of tethers extending through the central elongate structure, a cutting mechanism, a handle, and a control. The sheath is configured to slide over the central elongate structure. The cutting mechanism is configured to cut the tethers upon activation. The handle is connected to the central elongate structure. The control on the handle is configured to activate the cutting mechanism.

This and other embodiments can include one or more of the following features. The delivery device can further include an annular member including a plurality of pockets extending radially around the central elongate structure. Each of the tethers can include a feature on a distal end thereof configured to fit within a pocket of the plurality of pockets to hold the tether in place. A distal portion of the annular member can be configured to telescope relative to a proximal portion of the annular member. The delivery device can further include a second control on the handle configured to move the sheath proximally and distally over the central elongate structure. The cutting mechanism can include a resistive wire that is configured to be heated to cut the plurality of tethers. The delivery device can further include an o-ring configured to hold the plurality of tethers against the resistive wire. The resistive wire can be positioned within an annular member configured to hold distal ends of the plurality of tethers. The cutting mechanism can include a resistive plate that is configured to be heated to cut the plurality of tethers. The resistive plate can include a plurality of holes therethrough. Each tether can be configured to pass through a hole of the plurality of holes. The delivery device can further include an o-ring configured to hold the plurality of tethers against the resistive wire. The plurality of tethers can be made of polyether ether ketone or ultra-high molecular weight polyethylene. The cutting element can be a metallic ring or coil. The cutting element can be a resistive heating element. The resistive heating element can be configured to heat the plurality of tethers to a temperature of greater than 190° F. The cutting element can be a rotatable grinder. The cutting element can be a rotatable blade. The delivery device can further include a coiled spring configured to place tension on the plurality of tethers.

In general, in one embodiment, a method of delivering a prosthetic mitral valve includes: (1) extending a prosthetic delivery device into a heart with the prosthetic mitral valve collapsed within a sheath of the delivery device; (2) sliding the sheath to expose a first anchor of the prosthetic valve, thereby allowing the anchor to self-expand to an expanded annular configuration on a first side of the mitral valve annulus; (3) loosening a plurality of tethers of the delivery device so as to allow a second anchor to self-expand to an expanded annular configuration on a second side of the mitral valve annulus, the expansion of the proximal anchor causing the first anchor to move towards the second anchor and capture tissue of the mitral valve annulus between the proximal anchor and the distal anchor; (4) cutting the tethers with a cutting mechanism of the delivery device to release the tethers from the second anchor; and (5) removing the delivery device from the heart.

This and other embodiments can include one or more of the following features. The cutting mechanism can include a resistive heating element, and cutting the tethers can include heating the resistive heating element. Cutting the tethers can include heating the tethers to a temperature of greater than 190° F. to melt and sever the tethers. The tethers can be melted and severed in less than 1 minute.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 4A and 4B are perspective view of a tether ends retainer.

FIGS. 12A-12G show various ways of attaching a resistive heating wire to a delivery device.

FIGS. 13A-13B show a grinding mechanism that can be used as part of a delivery device.

FIGS. 14A-14B show a razor mechanism that can be used as part of a delivery device.

FIGS. 15A-15D show a delivery device including a coiled spring to hold tethers in tension.

DETAILED DESCRIPTION

The delivery devices described herein can be used to deliver and deploy a wide variety of replacement heart valves, such as prosthetic valves adapted to be minimally invasively delivered. Exemplary prosthetic valves that can be delivered and deployed include the expandable prosthetic valves described in U.S. patent application Ser. No. 14/677,320, filed Apr. 2, 2015, in U.S. Pat. No. 8,870,948, in International Patent Application No. PCT/US2016/032550, filed May 13, 2016, titled "REPLACEMENT MITRAL VALVES," and in U.S. patent application Ser. No. 14/677,320, filed Apr. 2, 2015, titled "REPLACEMENT CARDIAC VALVES AND METHODS OF USE AND MANUFACTURE," all of which are incorporated by reference herein. For example, the delivery devices herein are configured to be able to delivery and deploy a replacement heart valve, such as a mitral valve, that includes distal and proximal anchors.

Figure 1A:
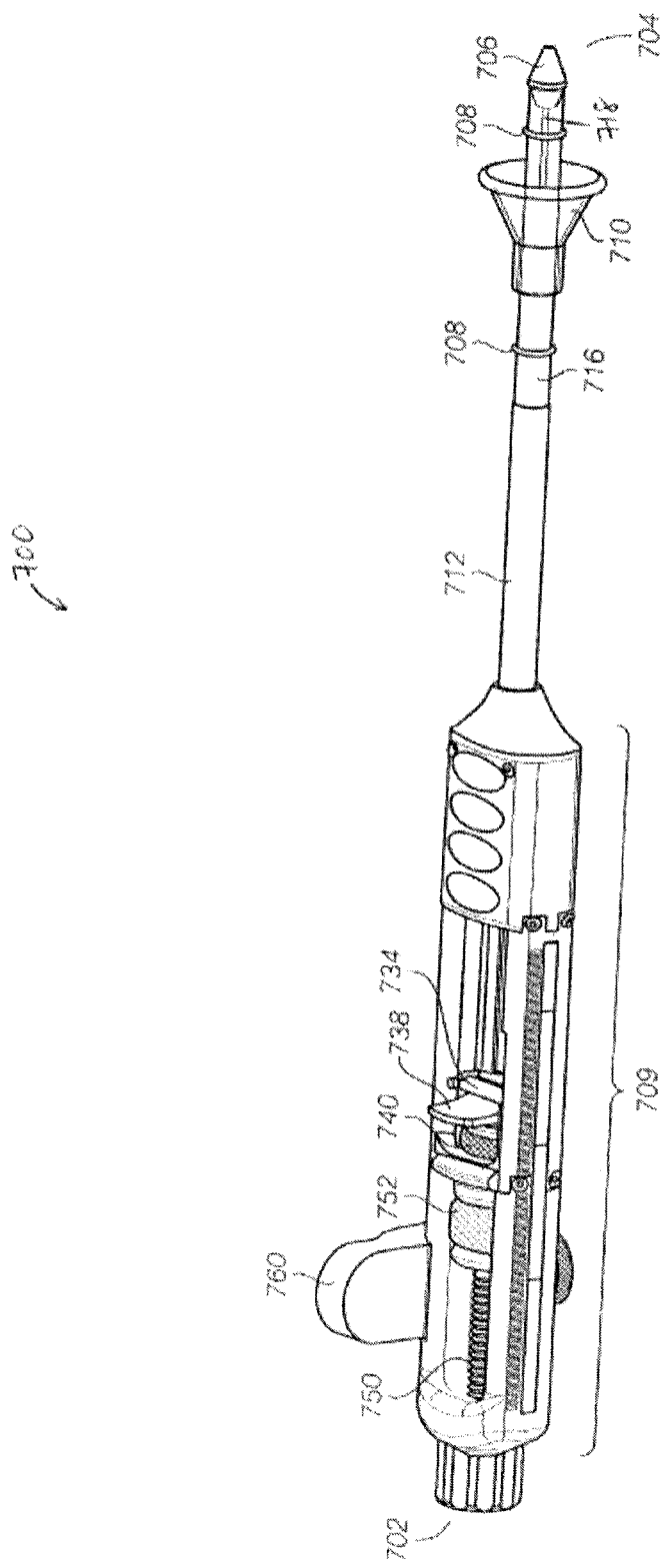
FIG. 1A is a perspective view of an exemplary delivery device.
Figure 1B:
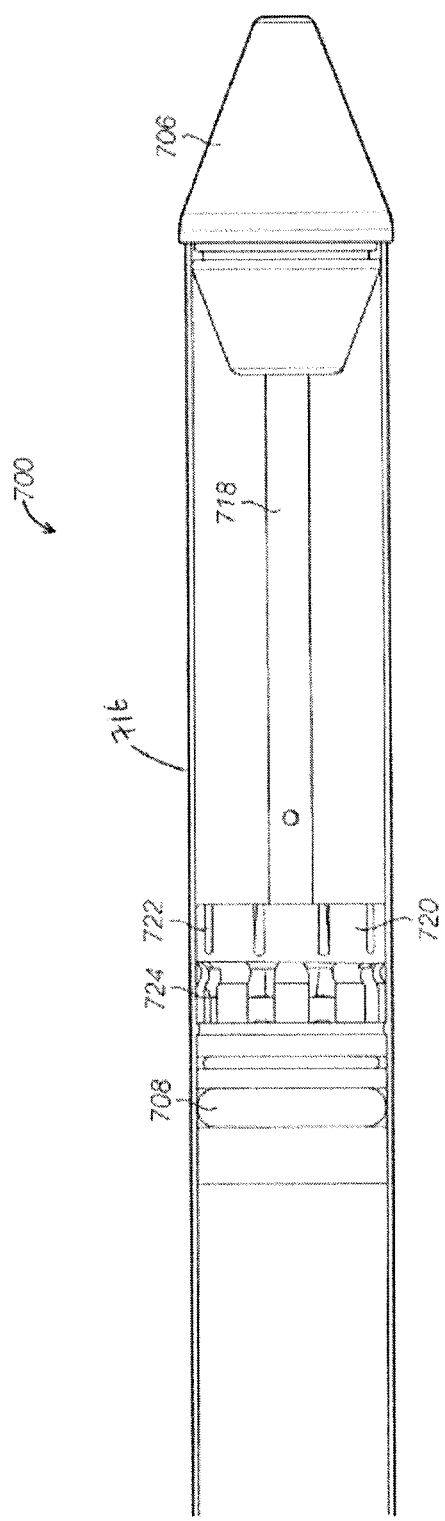
FIG. 1B is a close-up side view of the distal end of the delivery device of FIG. 1A.
Figure 1C:
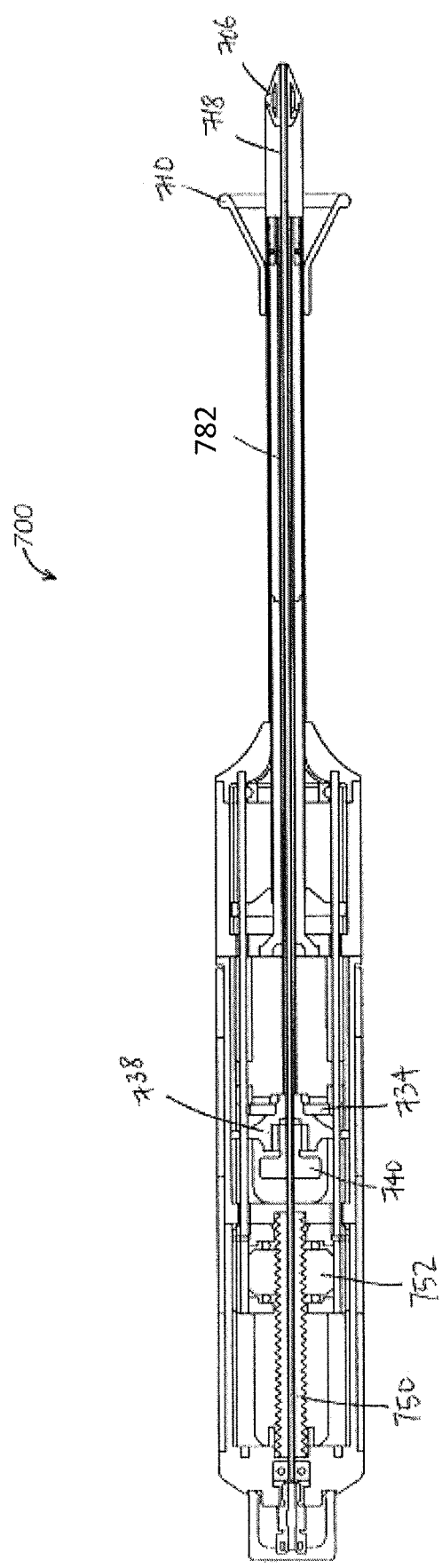
FIG. 1C is a cross-section of the delivery device of FIG. 1A.

FIGS. 1A-1C shows an embodiment of an exemplary prosthetic valve replacement delivery device 700. The delivery device 700 includes a device proximal end 702 and a device distal end 704. As can be seen from FIGS. 1A through 1C, the delivery device 700 has an elongated portion that terminates at a nosecone 706 at the device distal end 704. The nosecone 706 is coupled to a central stem 718, which is in turn coupled to a tether ends retainer 720. The elongated portion includes an outer sheath 712 and an inner sheath 716. The central stem 718 also couples to a series of tether/suture maintaining hypodermic tubes that are able to slide along the central stem 718. The inner sheath 716 is configured to slide relative to the central stem 718 (extend and retract) to cover or expose certain retaining features of the delivery device, e.g., the tether ends retainer 720 (see FIG. 1B), as well as aid with maintaining the prosthetic valve within the delivery device 700 prior to deployment. The device proximal end 702 includes a handle 709 for holding onto the delivery device. FIG. 1B shows a close-up of the distal end of the delivery device 700, where it is more apparent that the nosecone 706 is attached to the central stem 718 and the central stem 718 is coupled to a tether ends retainer 720. FIG. 1C shows a cross-sectional view of the delivery device 700.

Figure 2:
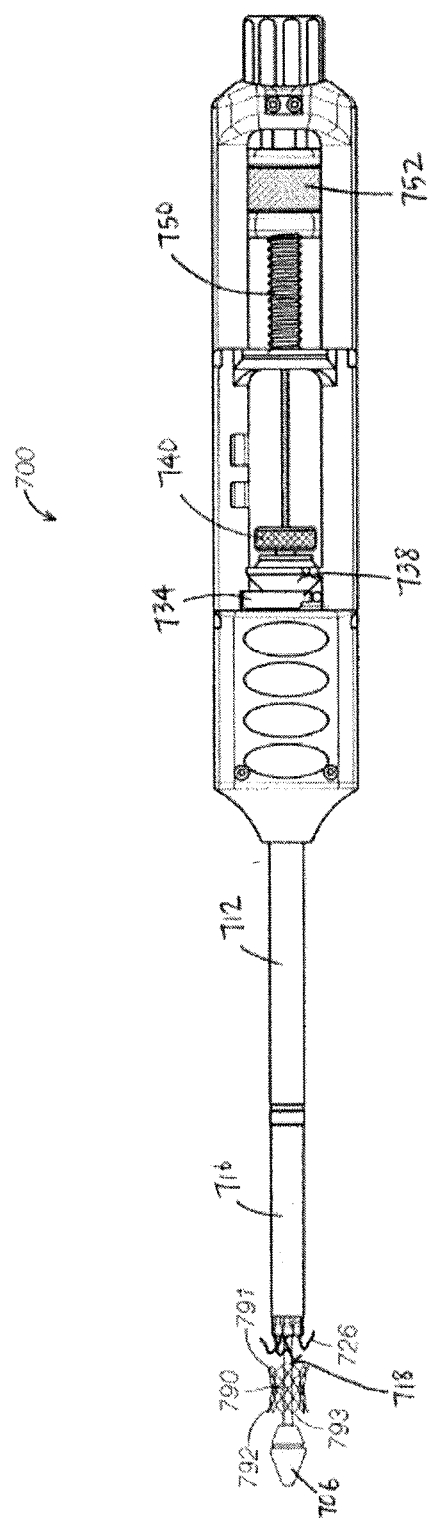
FIG. 2 shows a mitral valve prosthesis in the delivery device of FIG. 1A.

Referring to FIG. 2, tethers 726 aid with maintaining the prosthetic valve within the device 700. Tethers 726 can be made, for example, of suture materials. The tethers 726 extend along and around the center stem 718, and each tether 726 threads through a separate tubular structure 782. The tether ends that couple to the tether retainer 720 can further include a feature, e.g., a sphere, for coupling the tether ends to the tether retainer 720. The distal ends of the tethers can be configured to loop through the proximal end of the prosthetic valve. The distal ends of the tethers, once looped through the proximal end of the valve, can be maintained by the tether retainer 720.

Figure 3A:
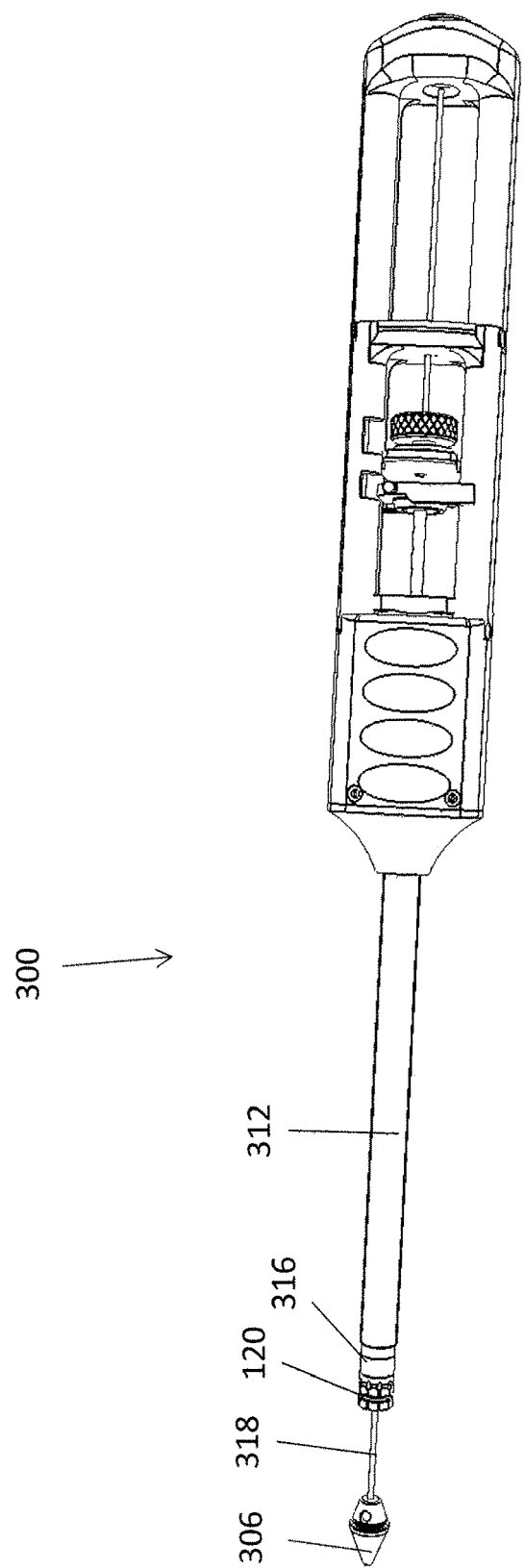
FIG. 3A is a perspective view of another exemplary delivery device.
Figure 3B:
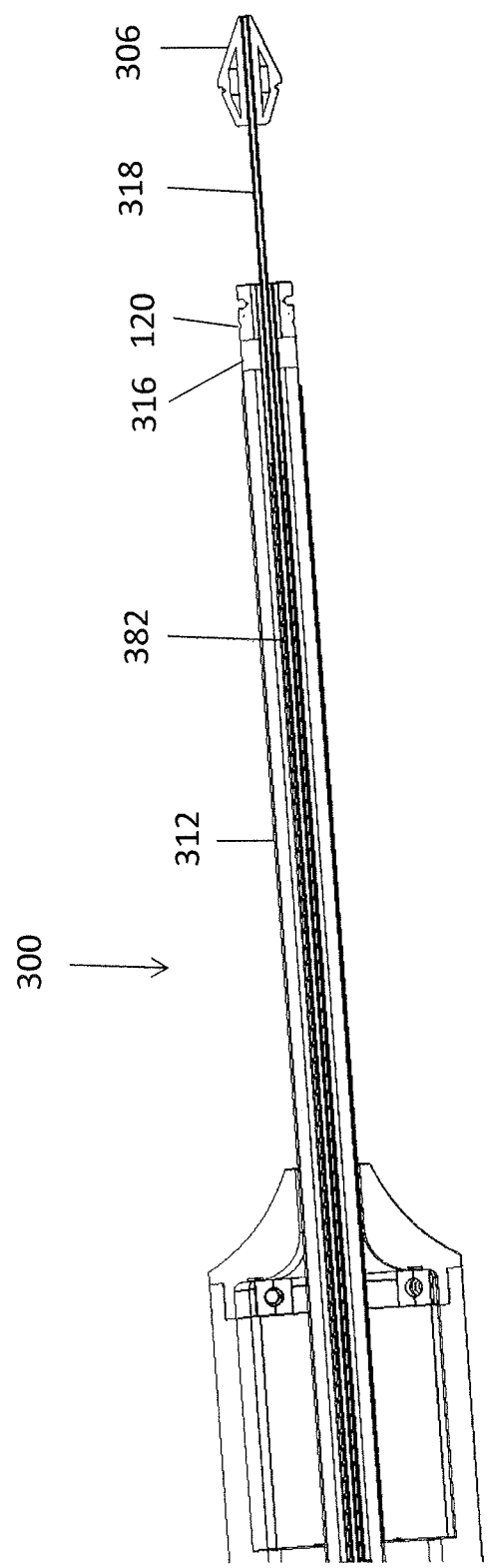
FIG. 3B is a close-up cross-section of the distal end of the delivery device of FIG. 3A.

Another exemplary delivery device 300 is shown in FIGS. 3A-3B. The device 300 is similar to device 700 and includes central stem 318 coupled to a tether ends retainer 120 and a distal nosecone 306. The central stem 318 also couples to a series of tether/suture maintaining hypodermic tubes 382 that are configured to slide along the central stem 318. An inner sheath 316 is configured to slide inside an outer sheath 312 and relative to the central stem 318 (extend and retract) to cover or expose certain retaining features of the delivery device, e.g., the tether ends retainer 120, as well as aid with maintaining the prosthetic valve within the delivery device 300 prior to deployment.

A close-up of the tether retainer 120 is shown in FIGS. 4A-4B. The tether retainer 120 includes a central channel 111 extending axially therethrough and series of tether pockets 124 extending around the outer circumference of the retainer 120. The tether pockets 124 are configured to hold the features at the distal end of the tethers 726. Thus, the tether pockets 124 can have shape that corresponds to the shape of the tether ends. For example, the pockets 124 can be spherical in shape so as to hold a spherical ball (from the distal end of a tether) therein. Further, an annular indent 122 can extend circumferentially around the tether retainer 120. Two holes 134a,b can extend from the central channel 111 to the annular ring 122. Moreover, the tether retainer 120 can include a groove 166 extending from each of the pockets 124 to the annular indent 122 and on to the distal end of the retainer 120.

Figure 4C:
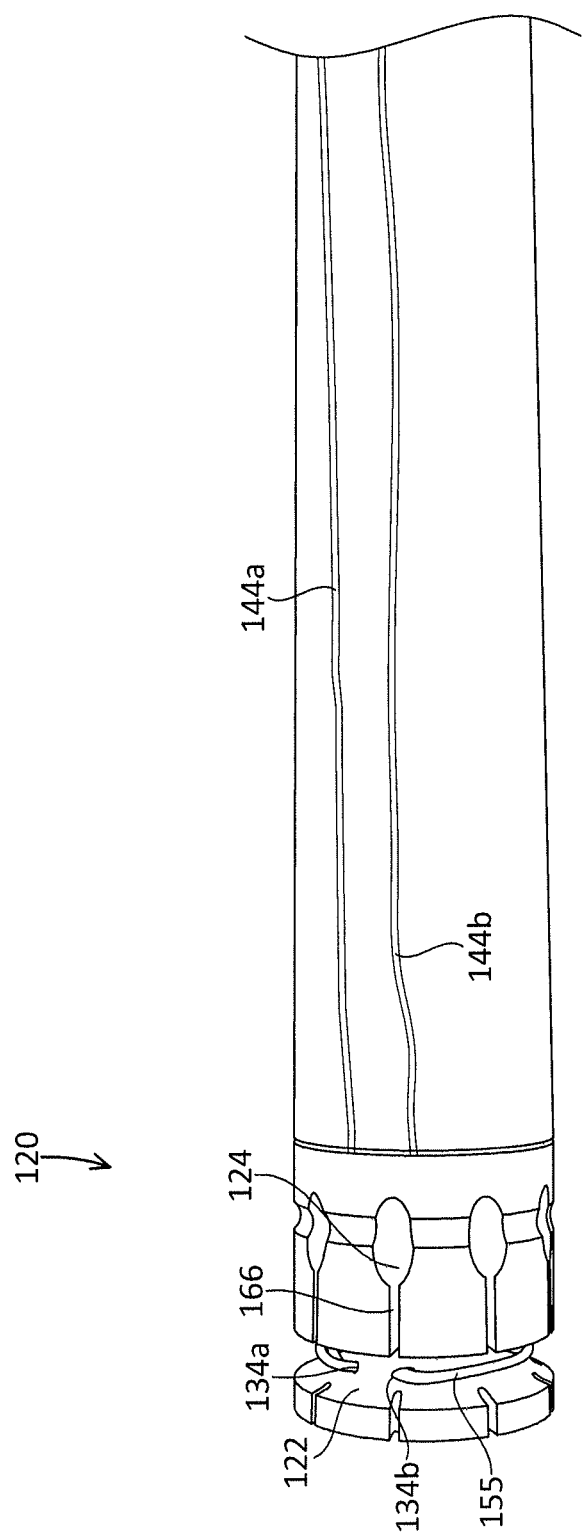
FIG. 4C shows a resistive wire around the tether ends retainer of FIGS. 4A-4B.
Figure 4D:
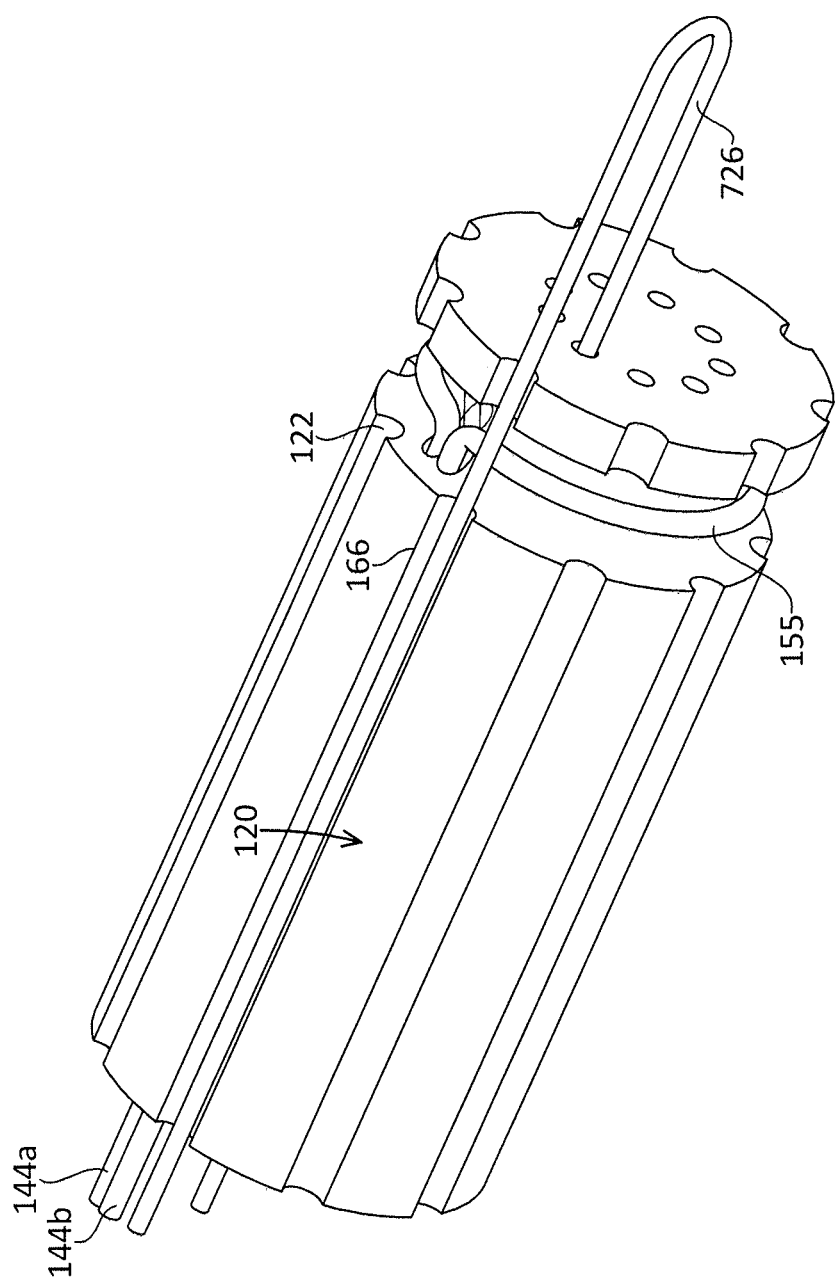
FIG. 4D shows a tether extending along the tether ends retainer and over the resistive wire.

Referring to FIG. 4C-4D, a pair of conductive wires 144a,b, e.g., copper wires, can extend through the inner diameter of the elongated portion or sheath of the delivery device, through the channel 111, and through the holes 134a,b. The conductive wires 144a,b can terminate in a resistive wire 155, such as Nichrome, that sits within the annular ring 122. Referring to FIG. 4D, a plurality of tethers 726 (only one is shown for clarity) can also extend through the inner diameter of the elongated portion of the delivery device and through the channel 111. The tethers 726 can extend out the distal end of the retainer 120 and then extend back through the channel 166 in the outer diameter of the retainer 120 and over the resistive wire 155. The distal ends of the tethers can be lodged within pockets to hold the ends in place, as described above. During use of the delivery device, an o-ring can be configured to sit over the resistive wire 155 within the annular ring 122 to hold the tethers thereon. When electricity is conducted through the wires 144a,b, it will flow to the resistive wire 155, which will heat up. The heat of the resistive wire 155 (against which the tethers sit) can cause the tethers to melt at the point of contact, thereby severing or cutting the distal ends of the tethers from the proximal ends of the tethers and allowing the delivery device to be removed from the valve while keeping the valve in place within the body (e.g., within the mitral valve annulus).

Figure 5A:
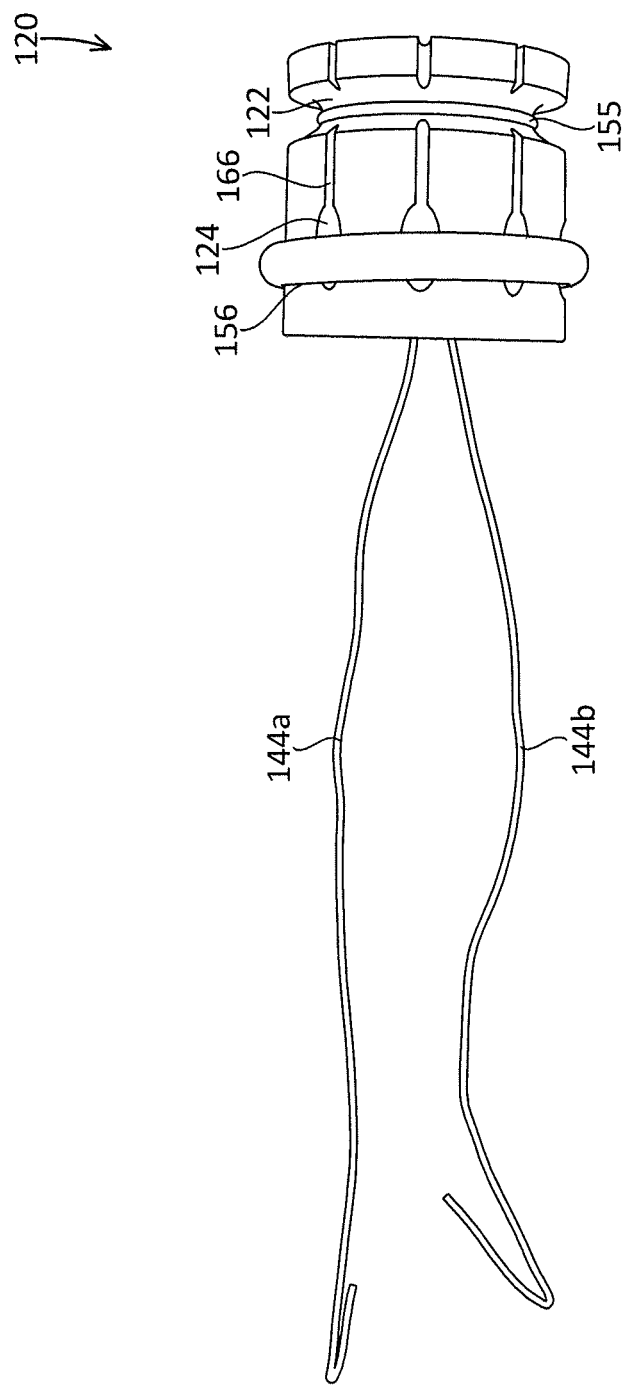
FIGS. 5A-5E show an exemplary method of loading tethers into a tether retainer that includes a resistive wire.
Figure 5B:
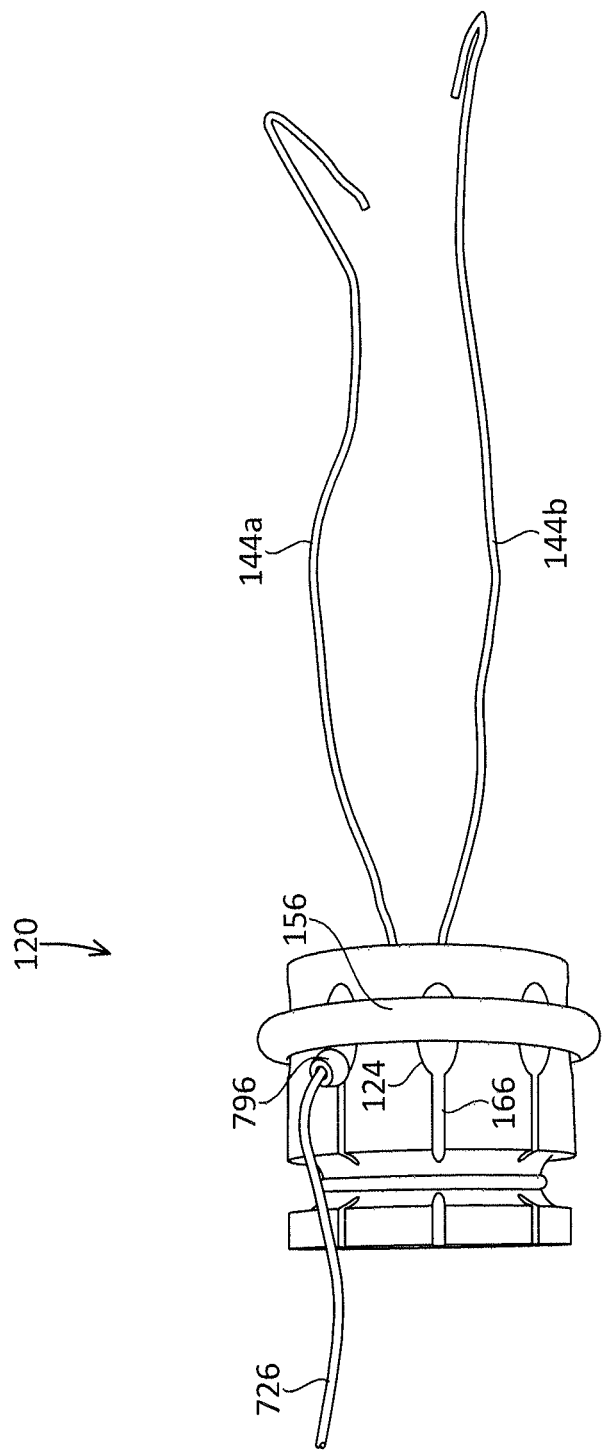
Figure 5C:
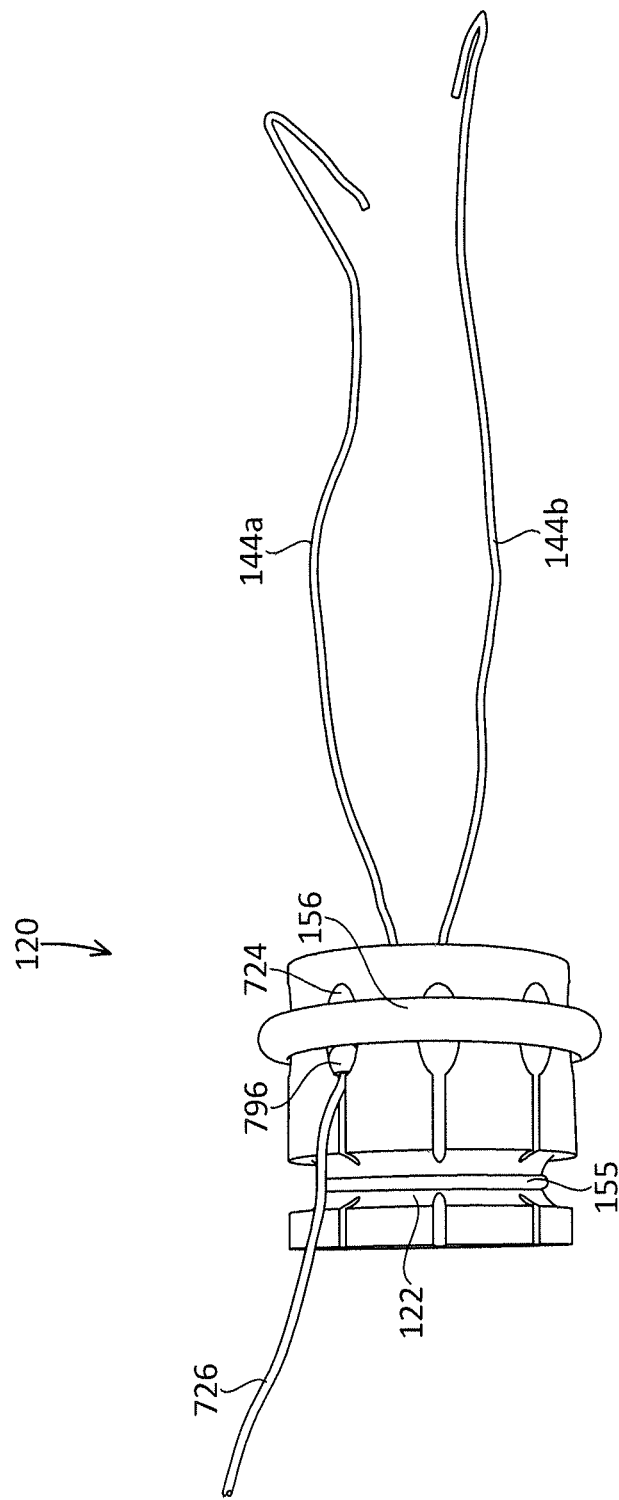
Figure 5D:
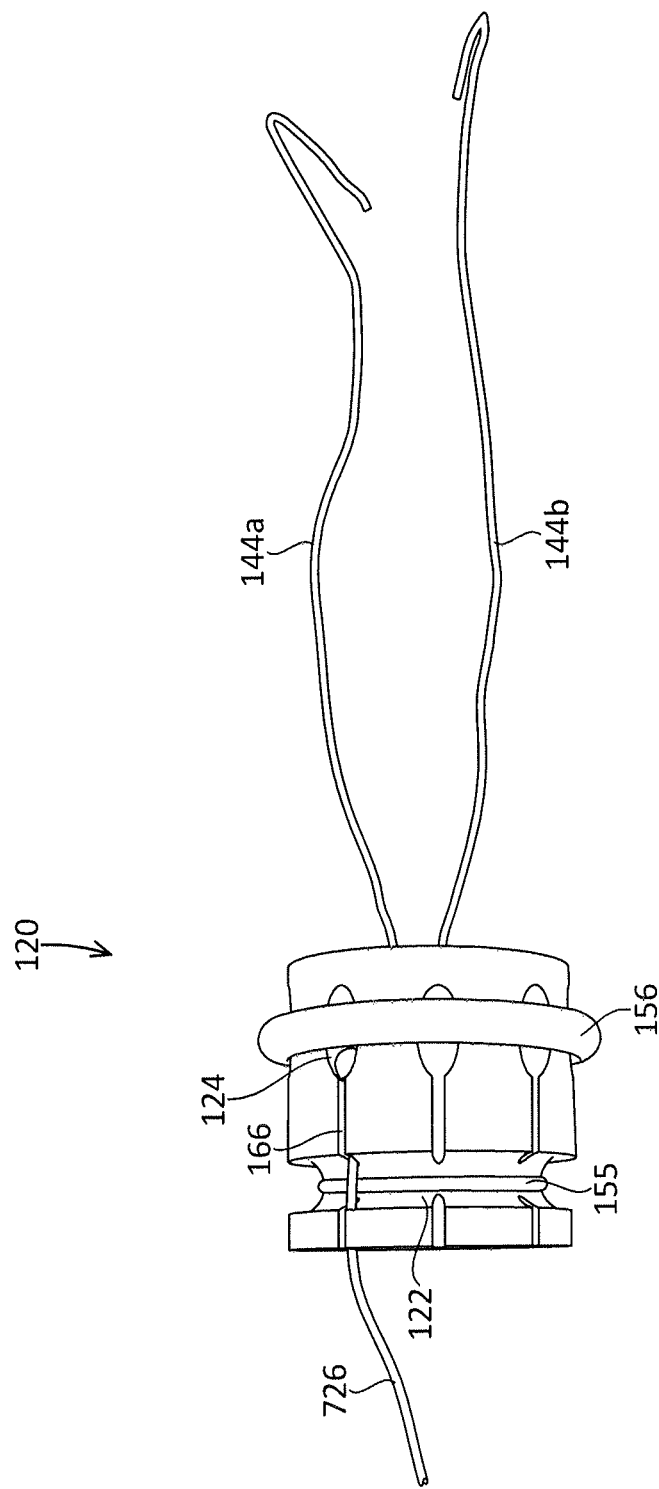
Figure 5E:
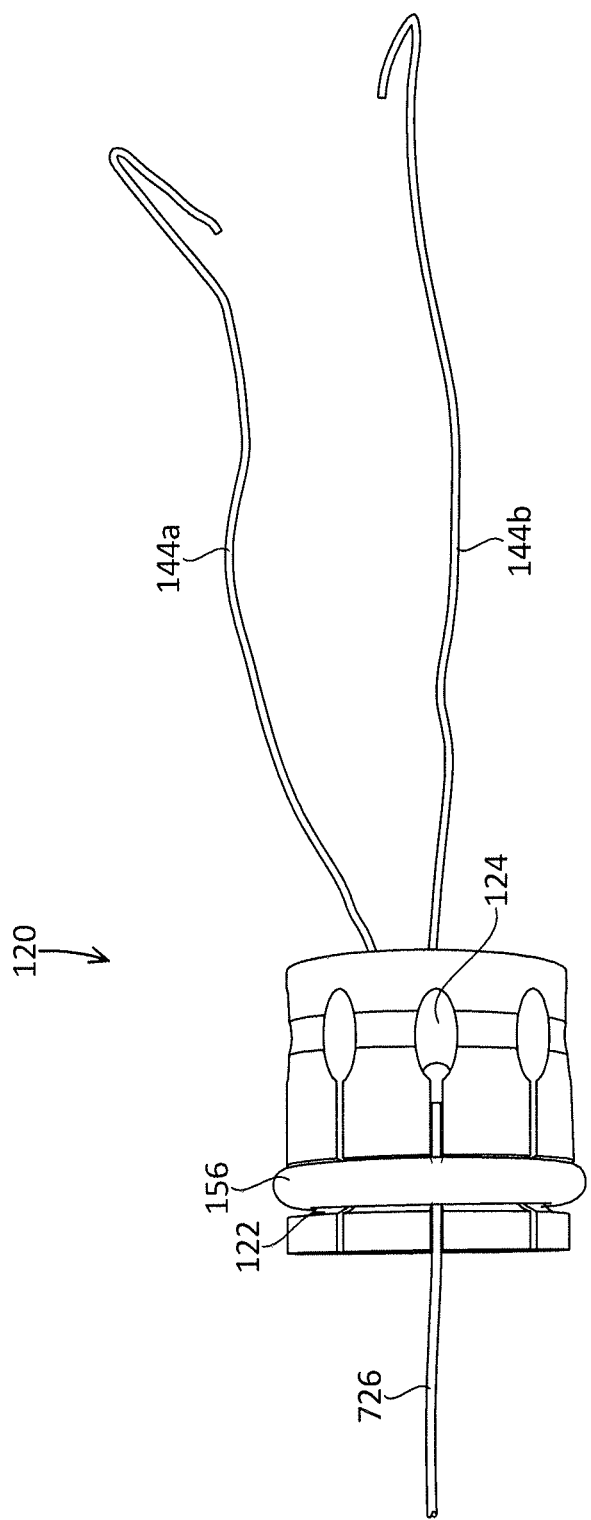

An exemplary method of loading tethers into the retainer 120 is shown in FIGS. 5A-5E. In FIG. 5A, the o-ring 156 can be moved to be positioned over the pockets 124. In FIG. 5B, a tether 726 (e.g., a UHMWPE suture) with a distal end feature 796 (e.g., a 1.5 mm tantalum ball) can be threaded through the inner diameter of the delivery device, out the distal end of the retainer 120, and positioned such that the distal end feature 796 is proximate to a pocket 124. In FIG. 5C, the feature 796 has been positioned partially inside of the pocket 124 and underneath the o-ring 156. In FIG. 5D, the feature 796 has been placed fully inside the pocket 124. In this position, the tether 726 runs within the groove 166 and sits against the resistive wire 155. In FIG. 5E, the o-ring 156 is moved into place within the annular indent 122, which presses the tether 726 firmly against the resistive wire 155. The o-ring 156 can also function to thermally and electrically insulate the resistive wire 155 from the blood stream.

Figure 6:
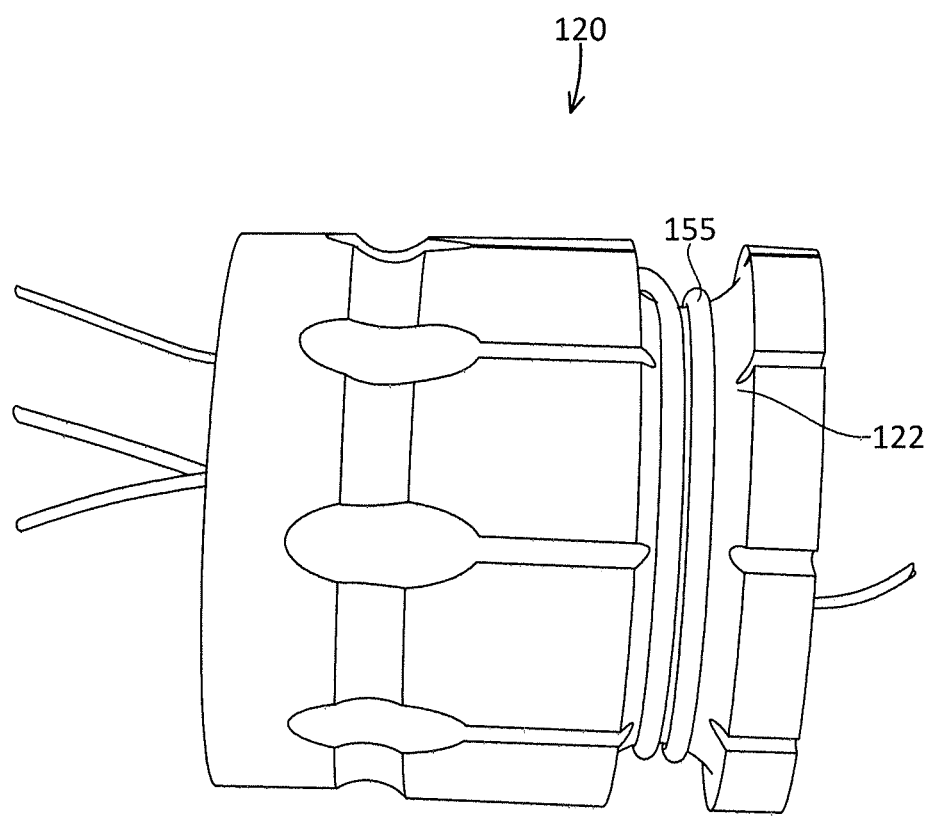
FIG. 6 is a perspective view of a tether ends retainer including a double loop of resistive wire therearound.

In some embodiments, referring to FIG. 6, the retainer 120 can include a double loop of resistive wire 155 extending therearound within the annular indent 122.

Figure 7A:
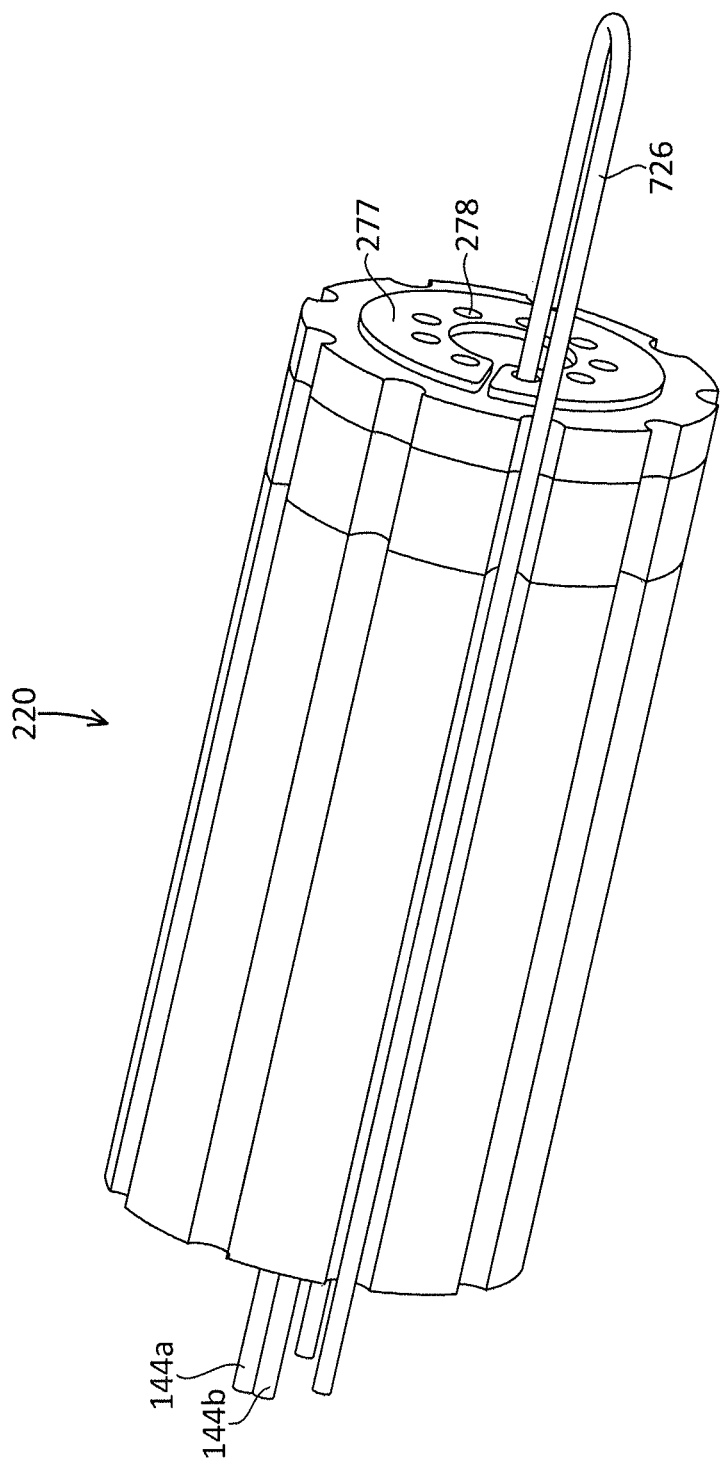
FIG. 7A shows a tether ends retainer including a resistive plate at the distal end.
Figure 7B:
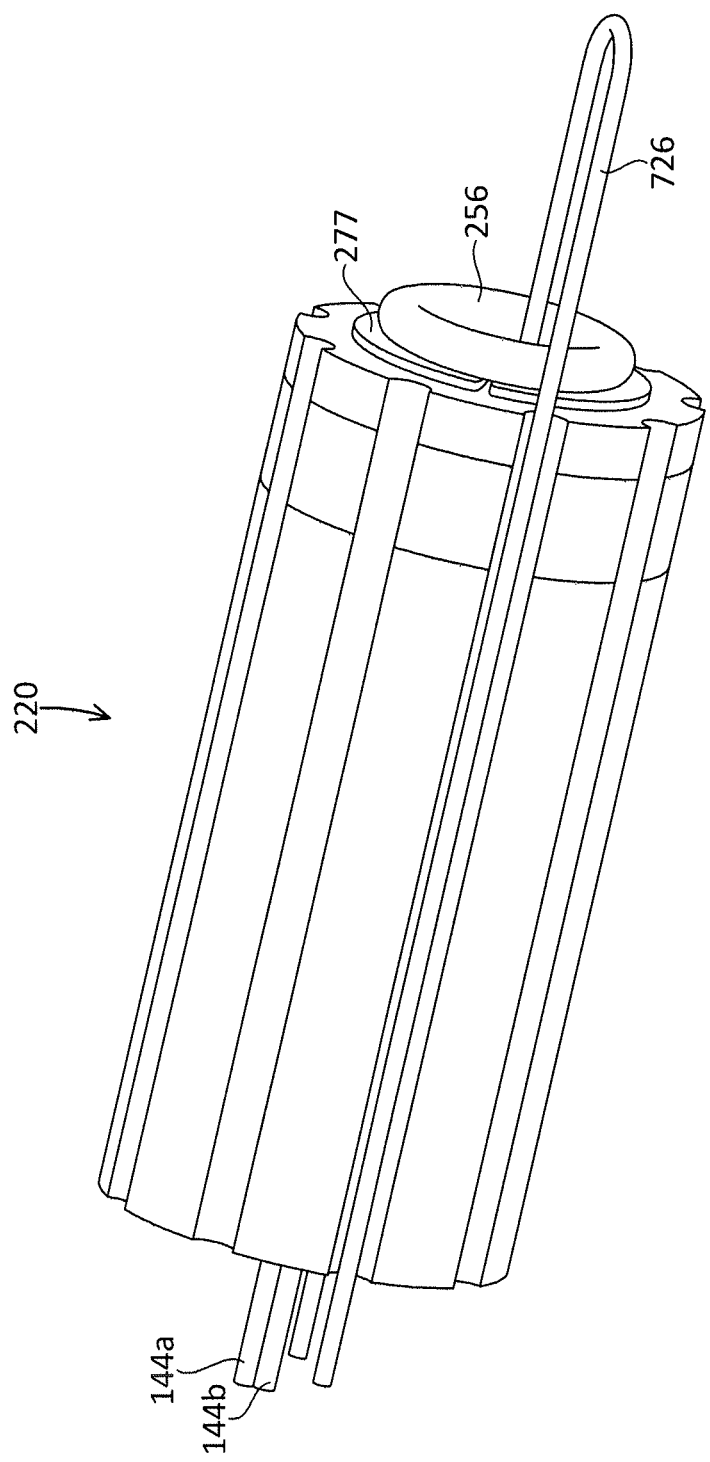
FIG. 7B shows the tether ends retainer of FIG. 7A with an o-ring thereover.

Referring to FIGS. 7A and 7B, in some embodiments, a tether retainer 220 can include a distal resistive plate 277 rather than a resistive wire. The plate 277 can include a plurality of holes 278 therein, such as around the circumference. Tethers 726 can be extended through the holes 278, and the distal end of each tether can be placed in a pocket, as described above. To release the tethers, the resistive plate 277 can be heated, causing the portion of the tethers touching the walls of the plate 277 to melt and sever. As shown in FIG. 7B, an o-ring 256 can be used to insulate the plate from the blood stream and/or to maintain the sutures in contact with the plate 277.

Figure 8:
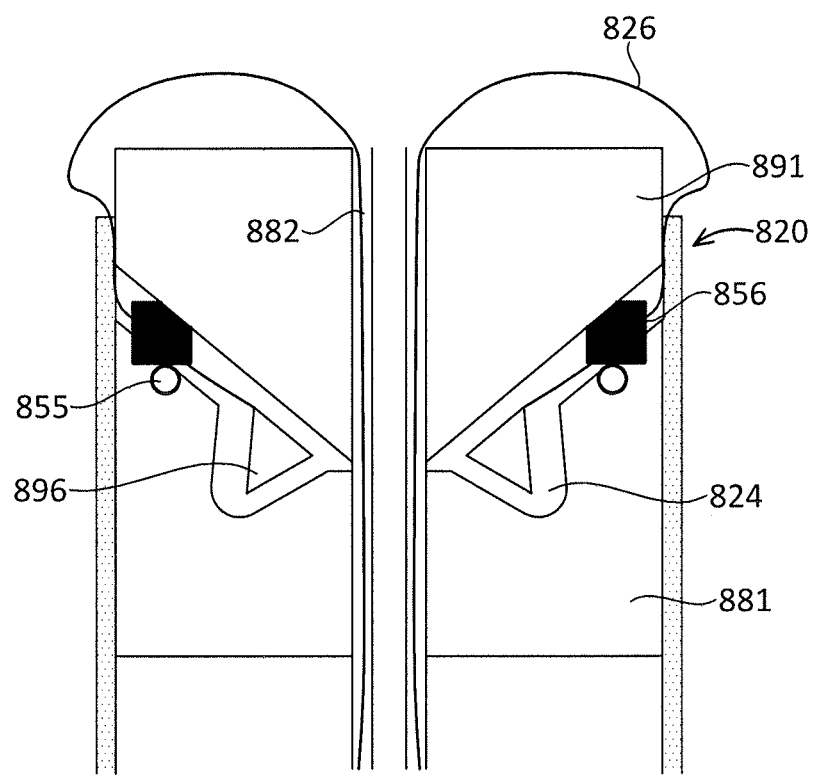
FIG. 8 shows a telescoping tether ends retainer.

Referring to FIG. 8, in some embodiments, a distal portion 891 tether retainer 820 can be configured to telescope relative to the proximal portion 881 of the retainer 820. Tethers 826 can extend along the length of the tether tubes 882, over the distal end of the retainer 820, and back into the pockets 824. Further, the distal portion 891 can move distally relative to the proximal portion 881 to allow the ends 896 of the tethers 826 to be positioned in the pockets 824 and then can be moved proximally again to hold the ends of the tethers 826 in place. The distal portion 891 can advantageously help place pressure on the tethers 826 to push them against the resistive wire 855. The distal portion 891 can further help isolate the resistive wire 855 from the blood during use to avoid shorting. An o-ring 856 can additionally shield the resistive wire 855 from the blood stream.

In some embodiments, the tether pockets can be designed or shaped so as to allow the distal ends of the tethers to be placed therein during loading of the valve on the delivery device, but can be designed so as to prevent the end of the tether from being removed during use.

In some embodiments, the retainers described herein can be made of polyether ether ketone (PEEK). In other embodiments, the retainers can be made of a ceramic, such as Macor.

Figure 9:
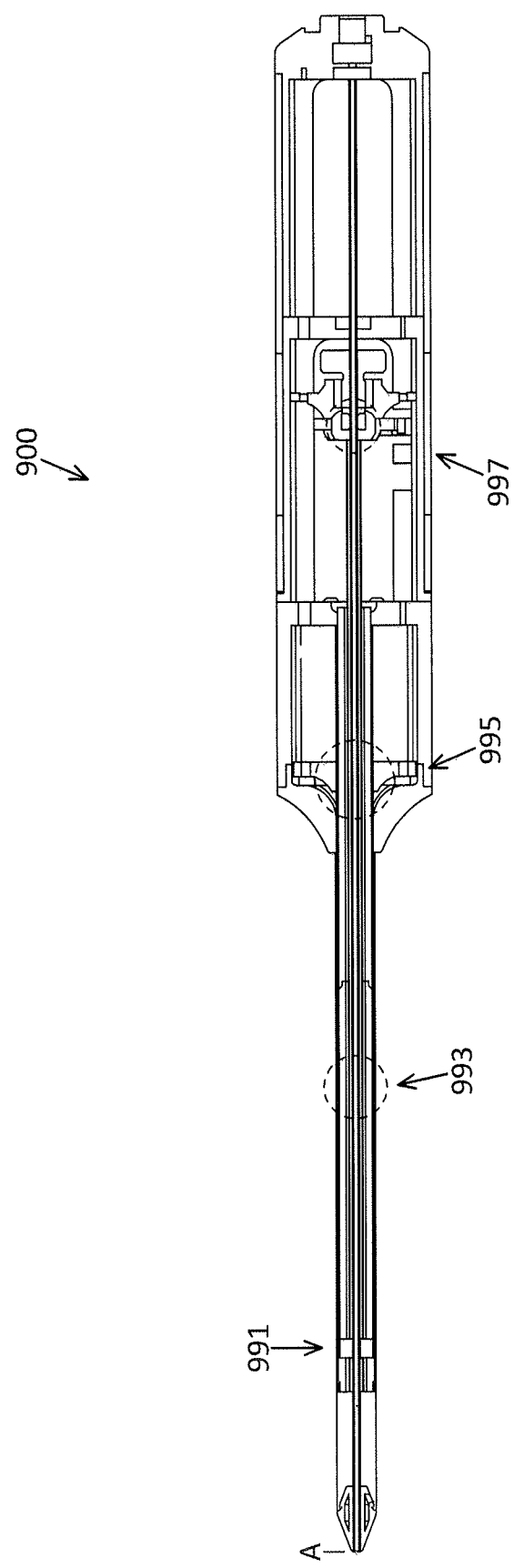
FIG. 9 shows a delivery device with various exemplary locations for placement of a resistive heating element.

The resistive heating element can be placed at various locations along the length of the device (i.e., it does not have to be part of the tether ends retainer and/or be located near the distal end of the shaft). For example, FIG. 9 shows a device 900 with various locations for the heating element. The heating element, for example, can be in a distal position at the tether ends retainer (location 991), mid-way along the shaft (location 993), at the distal end of the handle (location 995), or at the proximal end of the handle by the controls (location 997). In any or all of the locations, a shield jacket (e.g., made of ceramic) can be used to separate the heating element from the rest of the device and/or the blood.

Figure 10A:
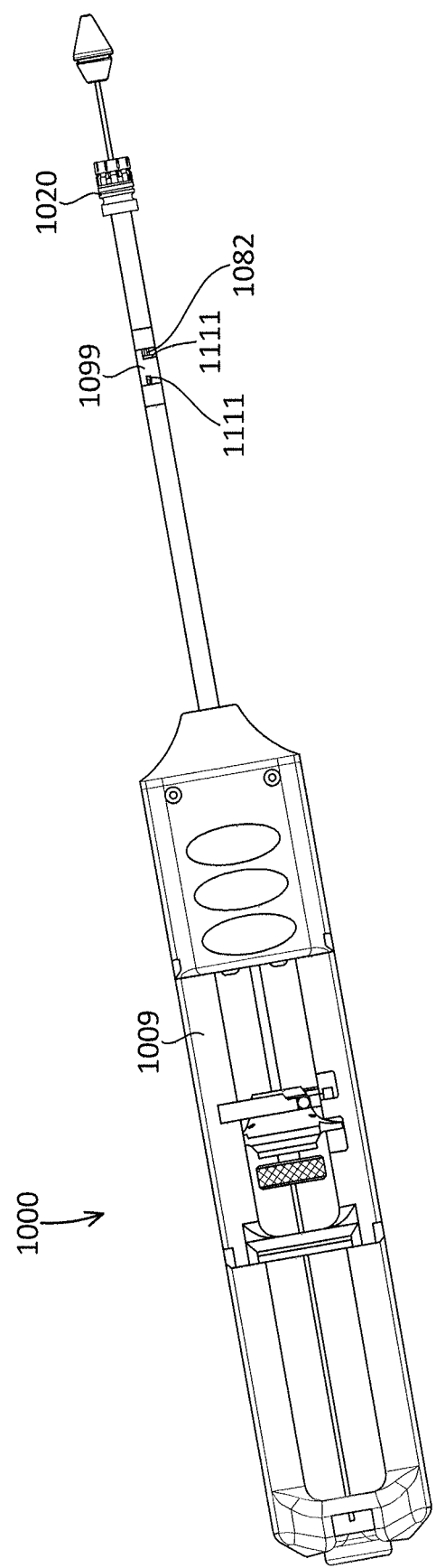
FIG. 10A shows a delivery device with a resistive heating element positioned along the mid-shaft.
Figure 10B:
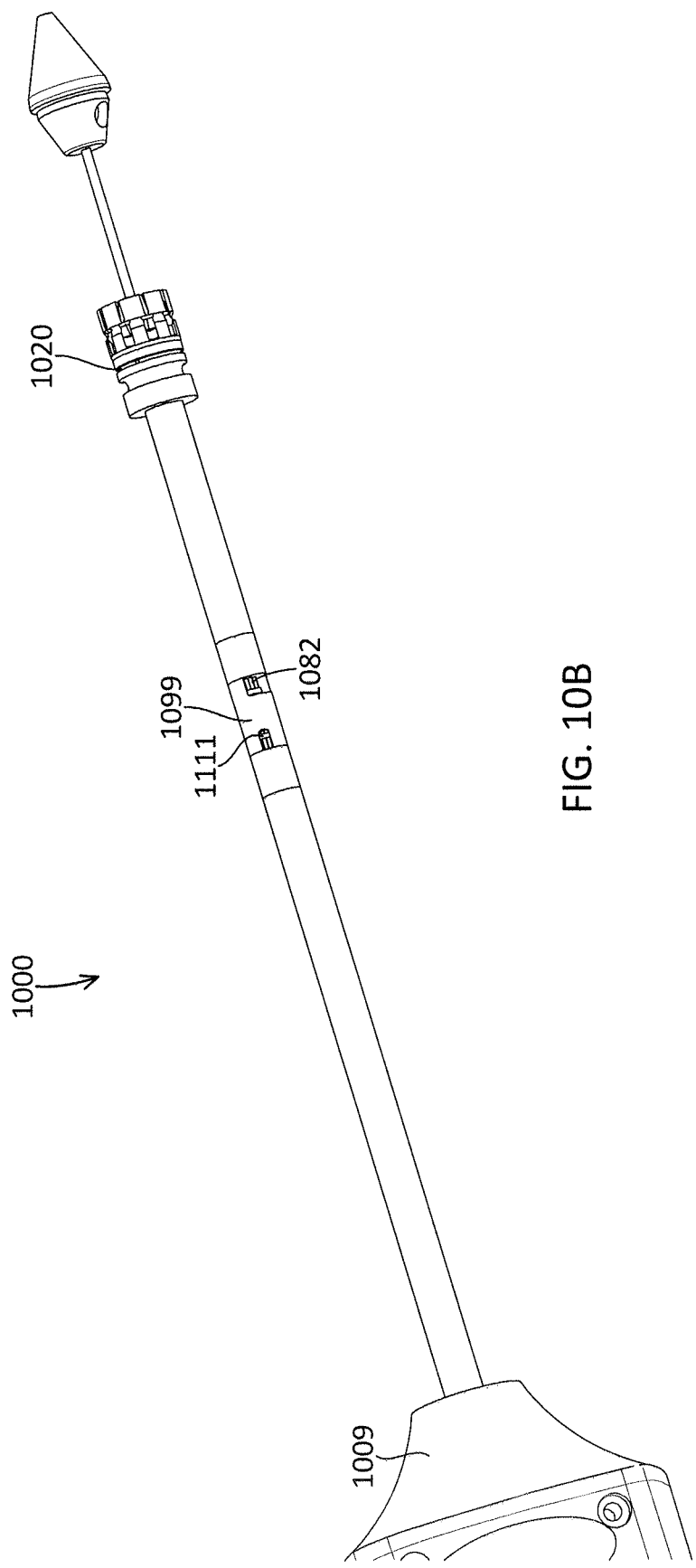
FIG. 10B is a close up of the distal end of the device of FIG. 10A.
Figure 10C:
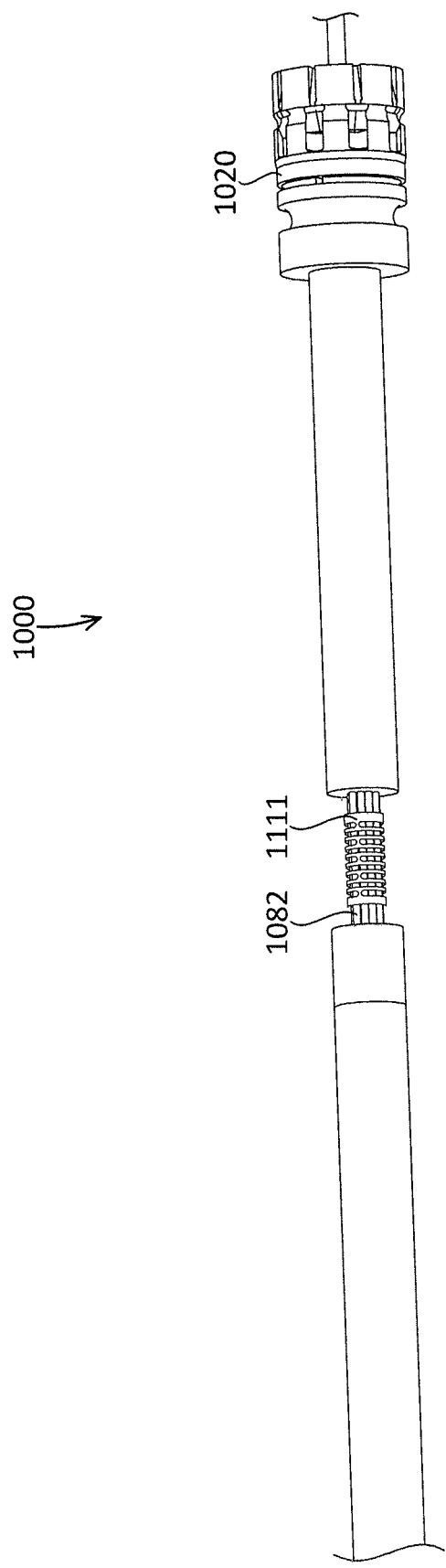
FIG. 10C is a close-up of the mid-shaft of the device of FIG. 10A with the outer portion removed so as to better view the resistive heating element.

An exemplary device 1000 having a resistive heating element 1111 positioned along the mid-shaft is shown in FIGS. 10A-10C. The resistive heating element 1111 is thus positioned between the handle 1009 and the tether ends retainer 1020. The resistive heating element 1111 can be, for example, a metallic cylindrical element with a plurality of notches, a notch coil, or a coil wire. Further, the heating element 1111 can be positioned circumferentially around the tether tubes 1082. Cylindrical ceramic elements 1099 can be positioned around the heating element 1111 and can be used to electrically shield the heating element 1111 from the rest of the shaft. A seal can further be used to isolate the heating element from fluid (i.e., to avoid shorting the heating element 1111). In some embodiments, the tether tubes 1082 can be actuated linearly (e.g., to move the tethers linearly) while the resistive heating element 1111 stays stationary. In other embodiments, the resistive heating element 1111 can move with the tubes 1082 (e.g., within a water tight housing). Because the resistive heating element 1111 is located along the mid-shaft rather than towards the distal end of the shaft, the heating element 1111 can advantageously be kept away from the heart during use of the device.

Figure 11A:
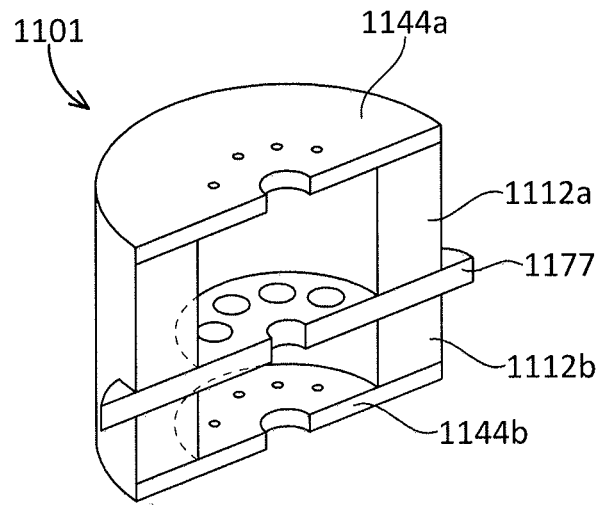
FIGS. 11A and 11B show a resistive cutting drum that can be used as part of a delivery device.
Figure 11B:
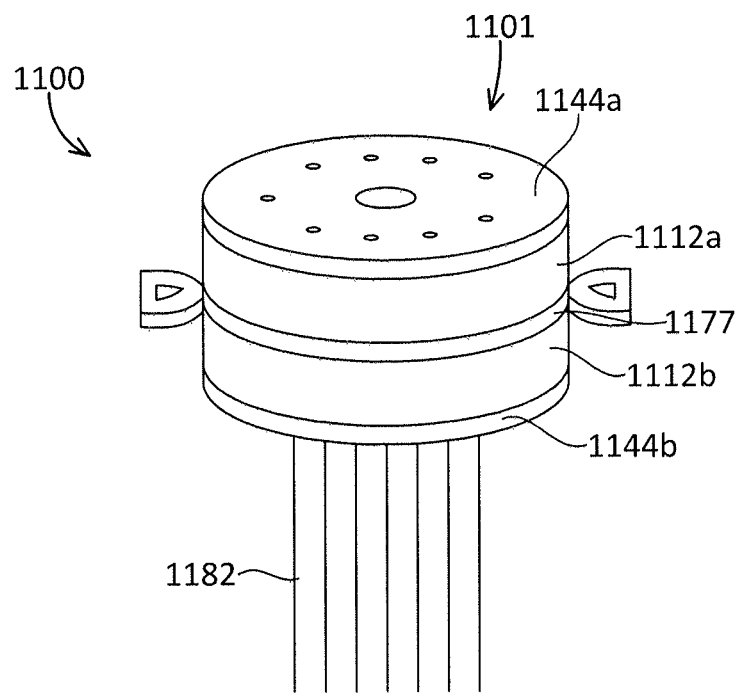

Another exemplary device 1100 is shown in FIGS. 11A-11B. The device 1100 includes a resistive cutting drum 1101 that is configured to be placed mid-way along the shaft that includes a resistive plate 1177 sandwiched by spacers 1112a,b (to electrically isolate the plate 1177). In some embodiments, the plate 1177 can further include a seal 1144a,b (e.g., silicone) on one or both ends to prevent fluid from contacting the plate 1177. The drum 1101 can further include a plurality of holes 1078 therein configured to allow the tethers to extend therethrough. In some embodiments, the resistive cutting drum 1101 can be configured to slide with the tether tubes 1182 to prevent having to move the tethers through the seals 1144a,b.

Figure 12E:
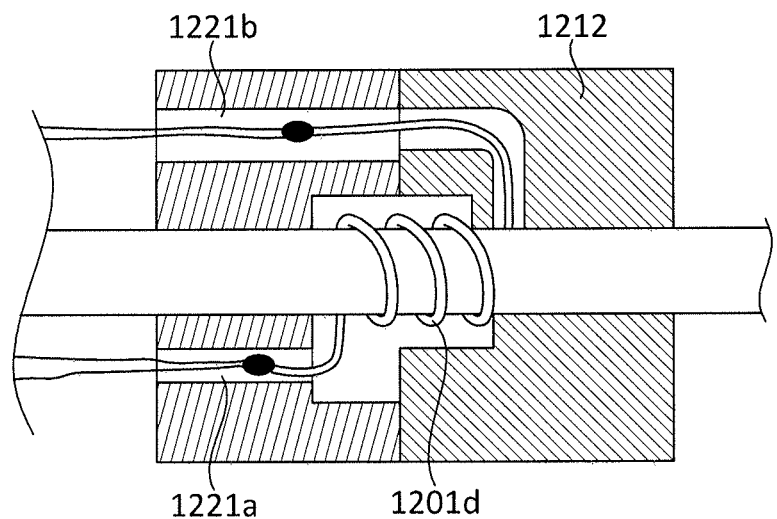
Figures 12F, 12G:
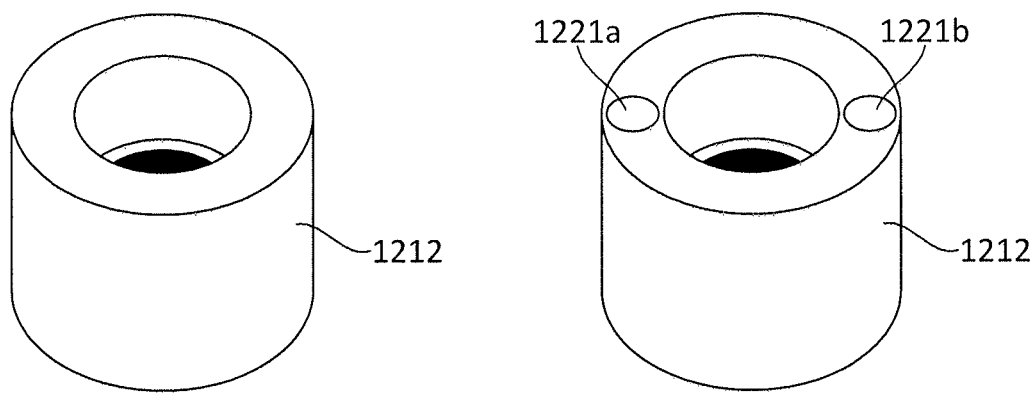

Referring to FIGS. 12A-12G, the resistive heating element(s) described herein can be attached to the delivery devices described herein in a variety of ways. For example, the resistive element 1201a can be wrapped or place directly against the tether tubes 1292, as shown in FIG. 12A. Alternatively, as shown in FIGS. 12B-12C, the resistive element 1201b can be wrapped around a large tube 1288 that then houses the smaller tether tubes therein. In some embodiments, referring to FIG. 12D, a slot 1289 can be formed in the outer diameter of the large tube 1288 to constrain the resistive element 1201c and get it closer to direct contact with the tether tubes 1292 (i.e., to make it easier to heat the tethers therein). Further, as shown in FIGS. 12E-G, in some embodiments, a jacket assembly 1212 can be used to shield the heating element 1201d from the rest of the catheter, and house wire junctions (e.g., in bores 1221a, b).

In some embodiments, the voltage applied to the conductive wires of the resistive heating elements described herein can be between 2-3V and the current can be between 2-4A.

One or more shield elements (such as ceramic elements 1099) can be used with any heating element described herein. The shield elements can help protect other elements of the delivery device while allowing a greater amount of power to be used to melt the tethers, thereby reducing the time that it takes to cut the tethers.

The tethers described herein for use with a resistive heating element can be a variety of materials that are subject to melting. For example, the tethers can be made of ultra-high molecular weight polyethylene.

In some embodiments, the heating elements used with the devices described herein can heat the tethers to a temperature of greater than 190° F., such as greater than 200° F., greater than 210° F., or greater than 220° F.

FIGS. 13A-15D show alternative mechanisms for cutting tethers that can be used in addition to or in place of the resistive heating elements described herein. For example, FIGS. 13A-13B show a grinding mechanism 1313 have a rotatable grinder 1315. The rotatable grinder 1315 can be positioned so as to push the tethers 1326 slightly radially outwards when not in use. As a result, when the grinder 1315 rotates, it can rotate against the tethers 1326 so as to slice therethrough. As shown, the tethers 1326 can still be positioned within tether tubes 1392, but the tether tubes 1392 can include a break therein at the rotatable grinder 1315.

FIGS. 14A-14B show a razor mechanism 1414 that can include a plurality of radially extending arms 1418 (see FIG. 14A; FIG. 14B does not show the arms 1418 for clarity) extending in the space 1490 between hypotubes 1492. The arms 1418 are designed to extend between each set of tethers 1426 until rotated. Once rotated, the arms 1418 can slice through the tethers 1426 (that extend out of the hypotubes 1492).

FIGS. 15A-15D show a delivery device 1500 including a sheath 1515, tether 1526, and a tether ends retainer 1520 (as described above). Further, the delivery device 1500 can include a razor cutting mechanism 1515 that can include a coiled spring 1520 configured to clamp the tethers 1526 either between the coils or against an inner or outer shaft. The spring 1520 can have a variable diameter so as to hold the tethers 1526 taught at a set location. A blade 1514 extending from the exterior thereof (FIG. 15A) or in the interior thereof (FIGS. 15B-D) can then be configured to rotate to cut through the tether 1526. In some embodiments, a spring actuator 1551 can be pulled back to unclamp the spring 1520 and release the tethers 1526. The spring mechanism can advantageously hold a set tension on the tethers 1526, which can aid in cutting of the tethers 1526.

In some embodiments, the methods for melting or cutting tethers described herein can cause severing within less than 2 minutes, such as less than 1 minute, less than 45 seconds, less than 30 seconds, less than 20 seconds, or less than 10 seconds.

The tether cutting mechanisms described herein can be used with other embodiments of delivery devices in addition to the specific delivery devices described herein. For example, the tether cutting mechanisms can be used as a component in addition to or in place of any component of any of the delivery devices described in U.S. PCT Application No. PCT/US16/32546, titled "CARDIAC VALVE DELIVERY DEVICES AND SYSTEMS," filed May 13, 2016, incorporated by reference herein.

The delivery devices described herein can advantageously be used to control the placement of the prosthetic valve at the mitral valve site, as described in U.S. PCT Application No. PCT/US16/32546, titled "CARDIAC VALVE DELIVERY DEVICES AND SYSTEMS," filed May 13, 2016, incorporated by reference herein.

Although described herein for use with a mitral valve prosthetic, the delivery systems described herein can be used with a variety of different implantable devices, including stents or other valve prosthetics.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A delivery device comprising:
   a central elongate structure;
   an annular member extending radially around the central elongate structure, a distal portion of the annular member being configured to telescope relative to a proximal portion of the annular member;
   a sheath configured to slide over the central elongate structure;
   a plurality of tethers extending through the central elongate structure;
   a tether cutter positioned within the sheath and configured to cut the plurality of tethers upon activation;
   a handle connected to the central elongate structure; and
   a control on the handle configured to activate the tether cutter.

2. The delivery device of claim 1, wherein the annular member includes a plurality of pockets extending radially around the central elongate structure, each of the tethers including a feature on a distal end thereof configured to fit within a pocket of the plurality of pockets to hold the tether in place.

3. The delivery device of claim 1, further comprising a second control on the handle configured to move the sheath proximally and distally over the central elongate structure.

4. The delivery device of claim 1, wherein the tether cutter includes a resistive wire that is configured to be heated to cut the plurality of tethers.

5. The delivery device of claim 4, further comprising an o-ring configured to hold the plurality of tethers against the resistive wire.

6. The delivery device of claim 4, wherein the resistive wire is positioned within an annular member configured to hold distal ends of the plurality of tethers.

7. The delivery device of claim 1, wherein the plurality of tethers are made of polyether ether ketone or ultra-high molecular weight polyethylene.

8. The delivery device of claim 1, wherein the tether cutter is a metallic ring or coil.

9. The delivery device of claim 1, wherein the tether cutter is a resistive heating element.

10. The delivery device of claim 9, wherein the resistive heating element is configured to heat the plurality of tethers to a temperature of greater than 190° F.

11. The delivery device of claim 1, further comprising a coiled spring configured to place tension on the plurality of tethers.

* * * * *